United States Patent
Chiu et al.

(10) Patent No.: US 11,963,868 B2
(45) Date of Patent: Apr. 23, 2024

(54) DOUBLE-SIDED ASPHERIC DIFFRACTIVE MULTIFOCAL LENS, MANUFACTURE, AND USES THEREOF

(71) Applicant: AST Products, Inc., Billerica, MA (US)

(72) Inventors: Yi-Feng Chiu, Hsinchu (TW); Chuan-Hui Yang, Taichung (TW); Wen-Chu Tseng, Westford, MA (US)

(73) Assignee: AST Products, Inc., Billerica, MA (US)

( * ) Notice: Subject to any disclaimer, the term of this patent is extended or adjusted under 35 U.S.C. 154(b) by 131 days.

(21) Appl. No.: 17/332,304

(22) Filed: May 27, 2021

(65) Prior Publication Data

US 2021/0369445 A1 Dec. 2, 2021

Related U.S. Application Data

(60) Provisional application No. 63/032,892, filed on Jun. 1, 2020.

(51) Int. Cl.
*A61F 2/16* (2006.01)

(52) U.S. Cl.
CPC ............ *A61F 2/164* (2015.04); *A61F 2/1618* (2013.01); *A61F 2/1654* (2013.01); *A61F 2002/1683* (2013.01); *A61F 2240/001* (2013.01)

(58) Field of Classification Search
CPC ...... A61F 2/164; A61F 2/1618; A61F 2/1654; A61F 2/1645; A61F 2002/1683;
(Continued)

(56) References Cited

U.S. PATENT DOCUMENTS

| 2,163,130 A | 6/1939 | Pellow |
| 4,402,579 A | 9/1983 | Poler |

(Continued)

FOREIGN PATENT DOCUMENTS

| AU | 2007219322 A1 | 10/2007 |
| AU | 2007219323 A1 | 10/2007 |

(Continued)

OTHER PUBLICATIONS

English Abstract of AU 2013200704-B2 published on Feb. 28, 2013.

(Continued)

*Primary Examiner* — Paul B Prebilic
(74) *Attorney, Agent, or Firm* — Morrison & Foerster LLP

(57) ABSTRACT

A double-sided aspheric diffractive multifocal lens and methods of manufacturing and design of such lenses in the field of ophthalmology. The lens can include an optic comprising an aspheric anterior surface and an aspheric posterior surface. On one of the two surfaces a plurality of concentric diffractive multifocal zones can be designed. The other surface can include a toric component. The double-sided aspheric surface design results in improvement of the modulation transfer function (MTF) of the lens-eye combination by aberration reduction and vision contrast enhancement as compared to one-sided aspheric lens. The surface having a plurality of concentric diffractive multifocal zones produces a near focus, an intermediate focus, and a distance focus.

15 Claims, 11 Drawing Sheets

(58) Field of Classification Search
CPC ........ A61F 2240/001; A61F 2250/0026; A61F 2250/0053
See application file for complete search history.

(56) References Cited

U.S. PATENT DOCUMENTS

| | | | |
|---|---|---|---|
| 4,450,593 A | 5/1984 | Poler | |
| 4,466,858 A | 8/1984 | Poler | |
| 4,473,434 A | 9/1984 | Poler | |
| 4,619,657 A | 10/1986 | Keates et al. | |
| 4,720,286 A | 1/1988 | Bailey et al. | |
| 4,846,913 A | 7/1989 | Frieder et al. | |
| 4,955,904 A | 9/1990 | Atebara et al. | |
| 4,981,342 A | 1/1991 | Fiala | |
| 4,995,714 A | 2/1991 | Cohen | |
| 4,995,715 A | 2/1991 | Cohen | |
| 5,017,000 A | 5/1991 | Cohen | |
| 5,037,485 A | 8/1991 | Chromecek et al. | |
| 5,044,743 A | 9/1991 | Ting | |
| 5,073,021 A | 12/1991 | Marron | |
| 5,106,180 A | 4/1992 | Marie et al. | |
| 5,121,979 A | 6/1992 | Cohen | |
| 5,142,411 A | 8/1992 | Fiala | |
| 5,144,483 A | 9/1992 | Cohen | |
| 5,158,572 A | 10/1992 | Nielsen | |
| 5,257,132 A | 10/1993 | Ceglio et al. | |
| 5,278,592 A | 1/1994 | Marie et al. | |
| 5,331,394 A | 7/1994 | Shalon et al. | |
| 5,344,447 A | 9/1994 | Swanson | |
| 5,410,375 A | 4/1995 | Fiala | |
| 5,517,260 A | 5/1996 | Glady et al. | |
| 5,623,322 A | 4/1997 | Hirschman et al. | |
| 5,682,223 A | 10/1997 | Menezes et al. | |
| 5,718,849 A | 2/1998 | Maus et al. | |
| 5,750,060 A | 5/1998 | Maus et al. | |
| 5,750,156 A | 5/1998 | Maus et al. | |
| 5,760,871 A | 6/1998 | Kosoburd et al. | |
| 5,782,911 A | 7/1998 | Herrick | |
| 5,806,530 A | 9/1998 | Herrick | |
| 5,821,943 A | 10/1998 | Shashua | |
| 5,838,496 A * | 11/1998 | Maruyama | G02B 5/1876 |
| | | | 359/569 |
| 5,855,605 A | 1/1999 | Herrick | |
| 5,861,934 A | 1/1999 | Blum et al. | |
| 5,875,017 A | 2/1999 | Ohnuma et al. | |
| 5,968,094 A | 10/1999 | Werbin et al. | |
| 5,982,543 A | 11/1999 | Fiala | |
| 6,010,215 A | 1/2000 | Miceli | |
| 6,024,902 A | 2/2000 | Maus et al. | |
| 6,068,464 A | 5/2000 | Su et al. | |
| 6,082,987 A | 7/2000 | Su et al. | |
| 6,086,203 A | 7/2000 | Blum et al. | |
| 6,099,763 A | 8/2000 | Su et al. | |
| 6,103,148 A | 8/2000 | Su et al. | |
| 6,106,118 A | 8/2000 | Menezes et al. | |
| 6,123,422 A | 9/2000 | Menezes et al. | |
| 6,139,145 A | 10/2000 | Israel | |
| 6,139,148 A | 10/2000 | Menezes | |
| 6,149,271 A | 11/2000 | Menezes et al. | |
| 6,199,984 B1 | 3/2001 | Menezes | |
| 6,231,184 B1 | 5/2001 | Menezes et al. | |
| 6,288,846 B1 | 9/2001 | Stoner, Jr. | |
| D449,321 S | 10/2001 | Su | |
| 6,312,424 B1 | 11/2001 | Largent | |
| 6,357,875 B1 | 3/2002 | Herrick | |
| 6,358,280 B1 | 3/2002 | Herrick | |
| 6,364,483 B1 | 4/2002 | Grossinger et al. | |
| 6,365,074 B1 | 4/2002 | Su | |
| 6,390,623 B1 | 5/2002 | Kokonaski et al. | |
| 6,474,814 B1 | 11/2002 | Griffin | |
| 6,505,934 B1 | 1/2003 | Menezes | |
| 6,536,899 B1 | 3/2003 | Fiala | |
| 6,630,083 B1 | 10/2003 | Nunez et al. | |
| 6,638,304 B2 | 10/2003 | Azar | |
| 6,685,315 B1 | 2/2004 | De Carle | |
| 6,709,105 B2 | 3/2004 | Menezes | |
| 6,855,164 B2 | 2/2005 | Glazier | |
| 6,883,916 B2 | 4/2005 | Menezes | |
| 6,932,839 B1 | 8/2005 | Kamerling et al. | |
| 6,951,391 B2 | 10/2005 | Morris et al. | |
| 7,025,456 B2 | 4/2006 | Morris et al. | |
| 7,041,133 B1 | 5/2006 | Azar | |
| 7,073,906 B1 | 7/2006 | Portney | |
| 7,093,938 B2 | 8/2006 | Morris et al. | |
| 7,141,065 B2 | 11/2006 | Azar | |
| 7,144,423 B2 | 12/2006 | McDonald | |
| 7,152,975 B2 | 12/2006 | Ho et al. | |
| 7,156,516 B2 | 1/2007 | Morris et al. | |
| 7,159,983 B2 | 1/2007 | Menezes et al. | |
| 7,178,918 B2 | 2/2007 | Griffin | |
| 7,229,173 B2 | 6/2007 | Menezes | |
| 7,229,475 B2 | 6/2007 | Glazier | |
| 7,232,218 B2 | 6/2007 | Morris et al. | |
| 7,256,921 B2 | 8/2007 | Kumar et al. | |
| 7,261,736 B1 | 8/2007 | Azar | |
| 7,270,677 B2 | 9/2007 | Azar | |
| 7,281,795 B2 | 10/2007 | Sandstedt et al. | |
| 7,286,275 B2 | 10/2007 | Kumar et al. | |
| 7,331,668 B2 | 2/2008 | Azar et al. | |
| 7,334,892 B2 | 2/2008 | Goodall et al. | |
| 7,334,894 B2 | 2/2008 | Hillis et al. | |
| RE40,152 E | 3/2008 | Maus et al. | |
| 7,338,161 B2 | 3/2008 | Chauveau et al. | |
| 7,341,345 B2 | 3/2008 | Azar et al. | |
| 7,342,112 B2 | 3/2008 | Kumar et al. | |
| 7,344,244 B2 | 3/2008 | Goodall et al. | |
| 7,349,137 B2 | 3/2008 | Kumar et al. | |
| 7,349,138 B2 | 3/2008 | Kumar et al. | |
| 7,350,919 B2 | 4/2008 | Hillis et al. | |
| 7,359,104 B2 | 4/2008 | Kumar et al. | |
| 7,364,294 B2 | 4/2008 | Menezes | |
| 7,377,641 B2 | 5/2008 | Piers et al. | |
| 7,390,088 B2 | 6/2008 | Goodall et al. | |
| 7,394,585 B2 | 7/2008 | Kumar et al. | |
| 7,429,105 B2 | 9/2008 | Kumar et al. | |
| 7,318,642 B2 | 10/2008 | Menezes | |
| 7,441,894 B2 | 10/2008 | Zhang et al. | |
| 7,452,075 B2 | 11/2008 | Iuliano | |
| 7,457,025 B2 | 11/2008 | Kumar et al. | |
| 7,457,434 B2 | 11/2008 | Azar | |
| 7,465,415 B2 | 12/2008 | Wang et al. | |
| 7,466,469 B2 | 12/2008 | Kumar et al. | |
| 7,470,027 B2 | 12/2008 | Hillis et al. | |
| 7,471,436 B2 | 12/2008 | Kumar et al. | |
| 7,481,532 B2 | 1/2009 | Hong et al. | |
| 7,481,955 B2 | 1/2009 | Xiao | |
| 7,486,988 B2 | 2/2009 | Goodall et al. | |
| 7,505,189 B2 | 3/2009 | Kumar et al. | |
| 7,527,754 B2 | 5/2009 | Chopra | |
| 7,543,937 B2 | 6/2009 | Piers et al. | |
| 7,553,925 B2 | 6/2009 | Bojkova | |
| 7,556,381 B2 | 7/2009 | Kelch et al. | |
| 7,557,206 B2 | 7/2009 | Kumar et al. | |
| 7,560,124 B2 | 7/2009 | Kumar et al. | |
| 7,579,022 B2 | 8/2009 | Kumar et al. | |
| 7,582,749 B2 | 9/2009 | Kumar et al. | |
| 7,594,727 B2 | 9/2009 | Hillis et al. | |
| 7,623,295 B2 | 11/2009 | Sabeta | |
| 7,632,540 B2 | 12/2009 | Kumar et al. | |
| 7,641,337 B2 | 1/2010 | Altmann | |
| 7,655,002 B2 | 2/2010 | Myers | |
| 7,656,569 B2 | 2/2010 | Hillis et al. | |
| 7,666,510 B2 | 2/2010 | Stewart | |
| 7,687,597 B2 | 3/2010 | Bojkova | |
| 7,696,296 B2 | 4/2010 | Bojkova et al. | |
| 7,699,464 B2 | 4/2010 | Iuliano | |
| 7,717,558 B2 | 5/2010 | Hong et al. | |
| 7,728,949 B2 | 6/2010 | Clarke et al. | |
| 7,812,295 B2 | 10/2010 | Zalevsky et al. | |
| 7,819,523 B2 | 10/2010 | Shimojo | |
| 7,828,430 B2 | 11/2010 | Ballet et al. | |
| 7,828,431 B2 | 11/2010 | Ho et al. | |
| 7,832,857 B2 | 11/2010 | Levinson et al. | |
| 7,833,442 B2 | 11/2010 | Chen et al. | |

(56) References Cited

U.S. PATENT DOCUMENTS

| | | |
|---|---|---|
| 7,847,998 B2 | 12/2010 | Kumar et al. |
| 7,850,879 B2 | 12/2010 | Cheb et al. |
| 7,883,206 B2 | 2/2011 | Blum et al. |
| 7,888,436 B2 | 2/2011 | Szymanski et al. |
| 7,891,809 B2 | 2/2011 | Ballet et al. |
| 7,901,076 B2 | 3/2011 | Azar et al. |
| 7,906,214 B2 | 3/2011 | Seybert et al. |
| 7,910,019 B2 | 3/2011 | He et al. |
| 7,910,020 B2 | 3/2011 | He et al. |
| 7,926,940 B2 | 4/2011 | Blum et al. |
| 7,931,373 B2 | 4/2011 | Hillis et al. |
| 7,978,391 B2 | 7/2011 | Kumar et al. |
| 7,988,285 B2 | 8/2011 | Sandstedt et al. |
| 8,003,005 B2 | 8/2011 | He et al. |
| 8,038,711 B2 | 10/2011 | Clarke |
| 8,077,373 B2 | 12/2011 | Kumar et al. |
| 8,084,133 B2 | 12/2011 | Colton |
| 8,089,678 B2 | 1/2012 | Kumar et al. |
| 8,100,527 B2 | 1/2012 | Hong et al. |
| 8,104,892 B2 | 1/2012 | Hillis et al. |
| 8,109,632 B2 | 2/2012 | Hillis et al. |
| 8,153,344 B2 | 4/2012 | Faler et al. |
| 8,211,338 B2 | 7/2012 | He et al. |
| 8,215,770 B2 | 7/2012 | Blum et al. |
| 8,216,308 B2 | 7/2012 | Blake et al. |
| 8,216,309 B2 | 7/2012 | Azar |
| 8,220,477 B2 | 7/2012 | Park |
| 8,231,217 B2 | 7/2012 | Ballet et al. |
| 8,235,525 B2 | 8/2012 | Lesage et al. |
| 8,240,850 B2 | 8/2012 | Apter et al. |
| 8,244,342 B2 | 8/2012 | Goodall et al. |
| 8,262,727 B2 | 9/2012 | McDonald |
| 8,262,728 B2 | 9/2012 | Zhang et al. |
| 8,267,515 B2 | 9/2012 | Azar et al. |
| 8,282,212 B2 | 10/2012 | Hillis et al. |
| 8,308,295 B2 | 11/2012 | Blum et al. |
| 8,319,937 B2 | 11/2012 | Clarke et al. |
| 8,349,210 B2 | 1/2013 | Xu et al. |
| 8,431,039 B2 | 4/2013 | Dia et al. |
| 8,434,865 B2 | 5/2013 | Blum et al. |
| 8,475,529 B2 | 7/2013 | Clake |
| 8,507,050 B2 | 8/2013 | Faler et al. |
| 8,518,546 B2 | 8/2013 | He et al. |
| 8,535,577 B2 | 9/2013 | Chopra et al. |
| 8,545,015 B2 | 10/2013 | Kumar et al. |
| 8,545,984 B2 | 10/2013 | He et al. |
| 8,556,416 B2 | 10/2013 | Lawu |
| 8,562,540 B2 | 10/2013 | Goodall et al. |
| 8,563,212 B2 | 10/2013 | Bowles et al. |
| 8,563,213 B2 | 10/2013 | Bowles et al. |
| 8,582,192 B2 | 11/2013 | Kumar et al. |
| 8,587,734 B2 | 11/2013 | Li |
| 8,608,800 B2 | 12/2013 | Portney |
| 8,613,868 B2 | 12/2013 | Dai et al. |
| 8,619,362 B2 | 12/2013 | Portney |
| 8,623,238 B2 | 1/2014 | Xu et al. |
| 8,628,685 B2 | 1/2014 | He et al. |
| 8,647,538 B2 | 2/2014 | Lu et al. |
| 8,649,081 B1 | 2/2014 | DeMeio et al. |
| 8,678,583 B2 | 3/2014 | Cohen |
| 8,698,117 B2 | 4/2014 | He et al. |
| 8,705,160 B2 | 4/2014 | He et al. |
| 8,747,466 B2 | 6/2014 | Weeber et al. |
| 8,779,168 B2 | 7/2014 | He et al. |
| 8,789,951 B2 | 7/2014 | Thompson et al. |
| 8,807,746 B2 | 8/2014 | Kato et al. |
| 8,828,284 B2 | 9/2014 | Carpenter |
| 8,828,296 B2 | 9/2014 | Zhang et al. |
| 8,828,507 B2 | 9/2014 | He et al. |
| 8,848,288 B2 | 9/2014 | Retsch, Jr. |
| 8,859,097 B2 | 10/2014 | Chopra |
| 8,871,016 B2 | 10/2014 | Trexler et al. |
| 8,882,264 B2 | 11/2014 | Bradley et al. |
| 8,885,139 B2 | 11/2014 | Peyghambarian et al. |
| 8,888,277 B2 | 11/2014 | Jubin et al. |
| 8,889,807 B2 | 11/2014 | Hickenboth et al. |
| 8,894,203 B2 | 11/2014 | Bradley et al. |
| 8,894,204 B2 | 11/2014 | Weeber et al. |
| 8,894,706 B2 | 11/2014 | Portney |
| 8,920,928 B2 | 12/2014 | He et al. |
| 8,926,091 B2 | 1/2015 | Kumar et al. |
| 8,992,610 B2 | 3/2015 | Blum et al. |
| 9,001,316 B2 | 4/2015 | Mohan et al. |
| 9,028,728 B2 | 5/2015 | Bancroft et al. |
| 9,029,532 B2 | 5/2015 | Dabideen et al. |
| 9,029,565 B1 | 5/2015 | He et al. |
| 9,030,740 B2 | 5/2015 | DeMeio et al. |
| 9,034,219 B2 | 5/2015 | He et al. |
| 9,040,648 B2 | 5/2015 | Hickenboth et al. |
| 9,045,647 B2 | 6/2015 | Kleyer et al. |
| 9,051,332 B1 | 6/2015 | He et al. |
| 9,051,426 B2 | 6/2015 | Hickenboth et al. |
| 9,062,213 B2 | 6/2015 | Bradford et al. |
| 9,081,208 B2 | 7/2015 | Blum et al. |
| 9,091,864 B2 | 7/2015 | Kingston et al. |
| 9,096,014 B2 | 8/2015 | Kumar et al. |
| 9,096,026 B2 | 8/2015 | Hall et al. |
| 9,101,466 B2 | 8/2015 | Hong |
| 9,116,363 B2 | 8/2015 | Pugh et al. |
| 9,122,083 B2 | 9/2015 | Blum et al. |
| 9,139,552 B2 | 9/2015 | Xiao et al. |
| 9,146,407 B2 | 9/2015 | Clarke et al. |
| 9,155,483 B2 | 10/2015 | Hillis et al. |
| 9,173,717 B2 | 11/2015 | Tripathi |
| 9,175,153 B2 | 11/2015 | Trexler et al. |
| 9,206,151 B2 | 12/2015 | He et al. |
| 9,216,080 B2 | 12/2015 | Bogaert et al. |
| 9,223,148 B2 | 12/2015 | Fiala et al. |
| 9,226,798 B2 | 1/2016 | Tripathi et al. |
| 9,259,309 B2 | 2/2016 | Fehr et al. |
| 9,259,310 B2 | 2/2016 | Schachar et al. |
| 9,277,988 B1 | 3/2016 | Chu |
| 9,279,907 B2 | 3/2016 | Bojkova |
| 9,304,329 B2 | 4/2016 | Zhao |
| 9,309,455 B2 | 4/2016 | He et al. |
| 9,320,594 B2 | 4/2016 | Schwiegerling |
| 9,323,073 B2 | 4/2016 | Pugh et al. |
| 9,332,899 B2 | 5/2016 | Shea et al. |
| 9,334,345 B2 | 5/2016 | Herold et al. |
| 9,334,439 B2 | 5/2016 | DeMeio et al. |
| 9,335,564 B2 | 5/2016 | Choi et al. |
| 9,405,041 B2 | 8/2016 | He et al. |
| 9,411,076 B2 | 8/2016 | Slezak et al. |
| 9,427,313 B2 | 8/2016 | Currie |
| 9,433,496 B2 | 9/2016 | Clough |
| 9,441,080 B2 | 9/2016 | Trexler et al. |
| 9,454,021 B2 | 9/2016 | Guillon et al. |
| 9,459,470 B2 | 10/2016 | Hillis et al. |
| 9,469,731 B2 | 10/2016 | Bojkova |
| 9,474,594 B2 | 10/2016 | Schachar et al. |
| 9,475,901 B2 | 10/2016 | Saha et al. |
| 9,523,004 B2 | 12/2016 | Hervieu et al. |
| 9,526,656 B2 | 12/2016 | Serdarevic et al. |
| 9,532,904 B2 | 1/2017 | Serdarevic et al. |
| 9,545,339 B2 | 1/2017 | Serdarevic et al. |
| 9,563,070 B2 | 2/2017 | Ando et al. |
| 9,568,643 B2 | 2/2017 | Bojkova et al. |
| 9,568,744 B2 | 2/2017 | Pugh et al. |
| 9,588,396 B2 | 3/2017 | Haddock et al. |
| 9,594,259 B2 | 3/2017 | Brennan et al. |
| 9,630,902 B2 | 4/2017 | He et al. |
| 9,658,471 B2 | 5/2017 | Ando et al. |
| 9,664,923 B2 | 5/2017 | Wildsmith et al. |
| 9,675,444 B2 | 6/2017 | Blum et al. |
| 9,690,021 B2 | 6/2017 | Turpen et al. |
| 9,693,679 B2 | 7/2017 | Dorronsoro Diaz et al. |
| 9,724,190 B2 | 8/2017 | Weeber et al. |
| 9,733,488 B2 | 8/2017 | Ambler et al. |
| 9,733,489 B2 | 8/2017 | Paille et al. |
| 9,770,326 B2 | 9/2017 | Bradley et al. |
| 9,782,064 B1 | 10/2017 | Linder et al. |
| 9,891,349 B2 | 2/2018 | Bojkova et al. |
| 9,895,260 B2 | 2/2018 | Schachar et al. |
| 9,927,633 B2 | 3/2018 | Franklin et al. |

(56) References Cited

U.S. PATENT DOCUMENTS

| | | |
|---|---|---|
| 9,955,862 B2 | 5/2018 | Freeman et al. |
| 9,963,546 B2 | 5/2018 | Bhagwager et al. |
| 9,987,127 B2 | 6/2018 | Bogaert et al. |
| 10,000,472 B2 | 6/2018 | He et al. |
| 10,005,763 B2 | 6/2018 | He et al. |
| 10,007,038 B2 | 6/2018 | Kumar et al. |
| 10,010,406 B2 | 7/2018 | Sandstedt et al. |
| 10,012,773 B2 | 7/2018 | Bojkova et al. |
| 10,012,848 B2 | 7/2018 | Brennan et al. |
| 10,039,635 B2 | 8/2018 | Wanders |
| 10,052,195 B2 | 8/2018 | Blum et al. |
| 10,061,143 B2 | 8/2018 | Brennan et al. |
| 10,085,833 B2 | 10/2018 | Piers et al. |
| 10,111,583 B1 | 10/2018 | Freeman et al. |
| 10,114,235 B2 | 10/2018 | Blum et al. |
| 10,145,996 B2 | 12/2018 | DeMeio et al. |
| 10,155,858 B2 | 12/2018 | Bhagwagar et al. |
| 10,175,508 B2 | 1/2019 | Ambier et al. |
| 10,185,057 B2 | 1/2019 | Colton et al. |
| 10,209,533 B2 | 2/2019 | Schwiegerling |
| 10,213,358 B2 | 2/2019 | Dorronsoro Diaz et al. |
| 10,219,893 B2 | 3/2019 | Currie et al. |
| 10,226,327 B2 | 3/2019 | Fernandez Gutierrez et al. |
| 10,278,809 B2 | 5/2019 | Gerlach |
| 10,278,810 B2 | 5/2019 | Clamen et al. |
| 10,278,811 B2 | 5/2019 | Choi et al. |
| 10,281,628 B2 | 5/2019 | Koenig, II et al. |
| 10,285,806 B2 | 5/2019 | Choi et al. |
| 10,295,841 B2 | 5/2019 | Ando |
| 10,302,968 B2 | 5/2019 | Waite et al. |
| 10,308,618 B2 | 6/2019 | Fromentin et al. |
| 10,342,700 B2 | 7/2019 | Schachar et al. |
| 10,371,866 B2 | 8/2019 | Frease et al. |
| 10,398,544 B2 | 9/2019 | Sayegh |
| 10,409,088 B2 | 9/2019 | Hillis et al. |
| 10,420,638 B2 | 9/2019 | Hong et al. |
| 10,423,061 B2 | 9/2019 | Tomasulo et al. |
| 10,426,599 B2 | 10/2019 | Choi et al. |
| 10,444,537 B2 | 10/2019 | Kumar et al. |
| 10,444,543 B2 | 10/2019 | Thompson |
| 10,463,474 B2 | 11/2019 | Lux et al. |
| 10,466,487 B2 | 11/2019 | Blum et al. |
| 10,473,822 B2 | 11/2019 | Fan et al. |
| 10,493,486 B2 | 12/2019 | Lynch et al. |
| 10,501,446 B2 | 12/2019 | He et al. |
| 10,501,477 B2 | 12/2019 | Deng et al. |
| 10,517,716 B2 | 12/2019 | Luque |
| 10,524,899 B2 | 1/2020 | Lux et al. |
| 10,532,997 B2 | 1/2020 | He et al. |
| 10,532,998 B2 | 1/2020 | He et al. |
| 10,543,577 B2 | 1/2020 | Masad et al. |
| 10,564,448 B2 | 2/2020 | Ando |
| 10,568,734 B2 | 2/2020 | Mackool |
| 10,571,611 B2 | 2/2020 | Koenig, II et al. |
| 10,590,220 B2 | 3/2020 | Saha et al. |
| 10,598,960 B2 | 3/2020 | Blum et al. |
| 10,619,018 B2 | 4/2020 | Kumar et al. |
| 10,619,098 B2 | 4/2020 | Reddy et al. |
| 10,646,329 B2 | 5/2020 | Zhao |
| 10,649,234 B2 | 5/2020 | Zhao |
| 10,670,885 B2 | 6/2020 | Zhao |
| 10,675,146 B2 | 6/2020 | Choi et al. |
| 10,688,522 B2 | 6/2020 | Lynch et al. |
| 10,698,234 B2 | 6/2020 | Zhao |
| 10,709,546 B2 | 7/2020 | Peyman |
| 10,712,589 B2 | 7/2020 | Zhao |
| 10,725,320 B2 | 7/2020 | Schwiegerling |
| 10,747,021 B2 | 8/2020 | Franklin et al. |
| 10,747,022 B2 | 8/2020 | Ando et al. |
| 10,765,510 B2 | 9/2020 | Sarver et al. |
| 10,786,959 B2 | 9/2020 | Damodharan et al. |
| 10,835,374 B2 | 11/2020 | Barzilay |
| 10,838,111 B2 | 11/2020 | Fromentin |
| 10,842,617 B2 | 11/2020 | Hong et al. |
| 10,849,736 B2 | 12/2020 | Neuhann et al. |
| 10,874,297 B1 | 12/2020 | Freeman et al. |
| 10,874,505 B2 | 12/2020 | Sandstedt et al. |
| 10,875,833 B2 | 12/2020 | Kumar et al. |
| 10,884,246 B2 | 1/2021 | Blum et al. |
| 10,884,288 B2 | 1/2021 | He et al. |
| 10,905,543 B2 | 2/2021 | Ghabra et al. |
| 10,912,457 B2 | 2/2021 | Schmeder |
| 10,932,901 B2 | 3/2021 | Zheleznyak et al. |
| 10,993,798 B2 | 5/2021 | Choi et al. |
| 10,994,563 B2 | 5/2021 | Frease et al. |
| 11,000,361 B2 | 5/2021 | Hong et al. |
| 11,000,365 B2 | 5/2021 | Choi et al. |
| 11,000,366 B2 | 5/2021 | Choi et al. |
| 11,009,723 B2 | 5/2021 | Ando |
| 11,029,536 B2 | 6/2021 | Lux et al. |
| 11,039,901 B2 | 6/2021 | Tripathi |
| 11,051,884 B2 | 7/2021 | Tripathi et al. |
| 11,076,987 B2 | 8/2021 | Schachar et al. |
| 11,084,236 B2 | 8/2021 | Turpen et al. |
| 11,103,344 B2 | 8/2021 | Zhang |
| 11,123,178 B2 | 9/2021 | Zhao |
| 11,129,707 B2 | 9/2021 | Pagnoulle et al. |
| 11,130,912 B2 | 9/2021 | Kumar et al. |
| 11,135,052 B2 | 10/2021 | Goldshleger et al. |
| 11,143,887 B2 | 10/2021 | Waite et al. |
| 2001/0027315 A1 | 10/2001 | Largent |
| 2002/0093701 A1 | 7/2002 | Zhang et al. |
| 2002/0101564 A1 | 8/2002 | Herrick |
| 2002/0196410 A1 | 12/2002 | Menezes |
| 2003/0018383 A1 | 1/2003 | Azar |
| 2003/0081171 A1 | 5/2003 | Griffin |
| 2003/0093149 A1 | 5/2003 | Glazier |
| 2003/0099330 A1 | 5/2003 | Mery et al. |
| 2003/0151831 A1 | 8/2003 | Sandstedt et al. |
| 2003/0187505 A1 | 10/2003 | Liao |
| 2004/0075807 A1 | 4/2004 | Ho et al. |
| 2004/0080711 A1 | 4/2004 | Menezes |
| 2004/0082995 A1 | 4/2004 | Woods |
| 2004/0199149 A1 | 10/2004 | Myers et al. |
| 2004/0252274 A1 | 12/2004 | Morris et al. |
| 2005/0003107 A1 | 1/2005 | Kumar et al. |
| 2005/0004361 A1 | 1/2005 | Kumar et al. |
| 2005/0012998 A1 | 1/2005 | Kumar et al. |
| 2005/0021138 A1 | 1/2005 | Woods |
| 2005/0021140 A1 | 1/2005 | Liao |
| 2005/0057720 A1 | 3/2005 | Morris et al. |
| 2005/0068493 A1 | 3/2005 | Menezes |
| 2005/0068494 A1 | 3/2005 | Griffin |
| 2005/0071002 A1 | 3/2005 | Glazier |
| 2005/0099597 A1 | 5/2005 | Sandstedt et al. |
| 2005/0140922 A1 | 5/2005 | Bekerman et al. |
| 2005/0168689 A1 | 8/2005 | Knox |
| 2005/0182490 A1 | 8/2005 | McDonald |
| 2005/0187622 A1 | 8/2005 | Sandstedt et al. |
| 2005/0259222 A1 | 11/2005 | Kelch et al. |
| 2005/0264757 A1 | 12/2005 | Morris et al. |
| 2006/0014099 A1 | 1/2006 | Faler et al. |
| 2006/0022176 A1 | 2/2006 | Wang et al. |
| 2006/0023162 A1 | 2/2006 | Azar et al. |
| 2006/0050234 A1 | 3/2006 | Morris et al. |
| 2006/0050236 A1 | 3/2006 | Menezes |
| 2006/0055883 A1 | 3/2006 | Morris et al. |
| 2006/0066808 A1 | 3/2006 | Blum et al. |
| 2006/0089713 A1 | 4/2006 | Azar |
| 2006/0092375 A1 | 5/2006 | Menezes et al. |
| 2006/0100704 A1 | 5/2006 | Blake et al. |
| 2006/0116764 A1* | 6/2006 | Simpson ............... A61F 2/1654 623/6.3 |
| 2006/0116765 A1 | 6/2006 | Blake et al. |
| 2006/0119793 A1 | 6/2006 | Hillis et al. |
| 2006/0119794 A1 | 6/2006 | Hillis et al. |
| 2006/0122530 A1 | 6/2006 | Goodall et al. |
| 2006/0122531 A1 | 6/2006 | Goodall et al. |
| 2006/0146281 A1 | 7/2006 | Goodall et al. |
| 2006/0164593 A1 | 7/2006 | Peyghambarian et al. |
| 2006/0176449 A1 | 8/2006 | Azar et al. |
| 2006/0203189 A1 | 9/2006 | Ho et al. |
| 2006/0206204 A1 | 9/2006 | Azar |
| 2006/0206205 A1 | 9/2006 | Azar |

(56) References Cited

U.S. PATENT DOCUMENTS

| | | |
|---|---|---|
| 2006/0224238 A1 | 10/2006 | Azar |
| 2006/0244906 A1 | 11/2006 | Piers et al. |
| 2006/0293747 A1 | 12/2006 | McDonald |
| 2007/0010757 A1 | 1/2007 | Goodall et al. |
| 2007/0019157 A1 | 1/2007 | Hillis et al. |
| 2007/0019272 A1 | 1/2007 | Hillis et al. |
| 2007/0019279 A1 | 1/2007 | Goodall et al. |
| 2007/0021831 A1 | 1/2007 | Clarke |
| 2007/0028931 A1 | 2/2007 | Hillis et al. |
| 2007/0030444 A1 | 2/2007 | Chauveau et al. |
| 2007/0030445 A1 | 2/2007 | Menezes |
| 2007/0041071 A1 | 2/2007 | Kumar et al. |
| 2007/0041073 A1 | 2/2007 | Kumar et al. |
| 2007/0047053 A1 | 3/2007 | Kumar et al. |
| 2007/0047054 A1 | 3/2007 | Kumar et al. |
| 2007/0047055 A1 | 3/2007 | Kumar et al. |
| 2007/0053047 A1 | 3/2007 | Kumar et al. |
| 2007/0053048 A1 | 3/2007 | Kumar et al. |
| 2007/0053049 A1 | 3/2007 | Kumar et al. |
| 2007/0053050 A1 | 3/2007 | Kumar et al. |
| 2007/0054131 A1 | 3/2007 | Stewart |
| 2007/0067030 A1 | 3/2007 | Glazier et al. |
| 2007/0075388 A1 | 4/2007 | Kumar et al. |
| 2007/0076167 A1 | 4/2007 | Kumar et al. |
| 2007/0098968 A1 | 5/2007 | Kumar et al. |
| 2007/0138448 A1 | 6/2007 | Chopra |
| 2007/0138665 A1 | 6/2007 | Chen et al. |
| 2007/0145337 A1 | 6/2007 | Chopra |
| 2007/0153231 A1 | 7/2007 | Iuliano |
| 2007/0177100 A1 | 8/2007 | Knox |
| 2007/0182917 A1 | 8/2007 | Zhang et al. |
| 2007/0182921 A1 | 8/2007 | Zhang et al. |
| 2007/0182924 A1* | 8/2007 | Hong .............. G02C 7/06 351/159.43 |
| 2007/0216863 A1 | 9/2007 | Menzes |
| 2007/0258143 A1 | 11/2007 | Portney |
| 2007/0260307 A1 | 11/2007 | Azar |
| 2007/0270548 A1 | 11/2007 | Bojkova et al. |
| 2007/0270549 A1 | 11/2007 | Szymanski et al. |
| 2007/0274626 A1 | 11/2007 | Sabeta |
| 2007/0275098 A1 | 11/2007 | Banks |
| 2007/0278460 A1 | 12/2007 | Xiao |
| 2007/0278461 A1 | 12/2007 | Petrovskaia et al. |
| 2007/0286969 A1 | 12/2007 | Nagpal et al. |
| 2007/0291345 A1 | 12/2007 | Kumar et al. |
| 2008/0045704 A1 | 2/2008 | Kumar et al. |
| 2008/0051575 A1 | 2/2008 | Kumar et al. |
| 2008/0086207 A1 | 4/2008 | Sandstedt et al. |
| 2008/0095933 A1 | 4/2008 | Colton et al. |
| 2008/0096023 A1 | 4/2008 | Colton et al. |
| 2008/0096048 A1 | 4/2008 | Kumar et al. |
| 2008/0096049 A1 | 4/2008 | Kumar et al. |
| 2008/0123172 A1 | 5/2008 | Kumar et al. |
| 2008/0125525 A1 | 5/2008 | Bojkova |
| 2008/0125570 A1 | 5/2008 | Bojkova |
| 2008/0137031 A1 | 6/2008 | Hillis et al. |
| 2008/0151183 A1 | 6/2008 | Altmann |
| 2008/0160318 A1 | 7/2008 | Senkfor et al. |
| 2008/0161673 A1 | 7/2008 | Goodall et al. |
| 2008/0180630 A1 | 7/2008 | Clarke et al. |
| 2008/0180803 A1 | 7/2008 | Seybert et al. |
| 2008/0187749 A1 | 8/2008 | Cael et al. |
| 2008/0198326 A1 | 8/2008 | Piers et al. |
| 2008/0198331 A1 | 8/2008 | Azar et al. |
| 2008/0206579 A1 | 8/2008 | LaLumere et al. |
| 2008/0212017 A1 | 9/2008 | Ballet et al. |
| 2008/0212023 A1 | 9/2008 | Bovet et al. |
| 2008/0218689 A1 | 9/2008 | Blum et al. |
| 2008/0231799 A1 | 9/2008 | Iuliano |
| 2008/0297720 A1 | 12/2008 | Ballet et al. |
| 2009/0033863 A1 | 2/2009 | Blum et al. |
| 2009/0082859 A1 | 3/2009 | Azar |
| 2009/0088840 A1* | 4/2009 | Simpson .............. G02C 7/044 623/6.11 |
| 2009/0096981 A1 | 4/2009 | Clarke et al. |
| 2009/0122262 A1 | 5/2009 | Hong et al. |
| 2009/0124721 A1 | 5/2009 | Chen et al. |
| 2009/0125105 A1 | 5/2009 | Lesage et al. |
| 2009/0135462 A1 | 5/2009 | Kumar et al. |
| 2009/0146104 A1 | 6/2009 | He et al. |
| 2009/0147378 A1 | 6/2009 | Zelevsky et al. |
| 2009/0187242 A1 | 7/2009 | Weeber et al. |
| 2009/0189830 A1 | 7/2009 | Deering et al. |
| 2009/0195751 A1 | 8/2009 | Hillis et al. |
| 2009/0204207 A1 | 8/2009 | Blum et al. |
| 2009/0239043 A1 | 9/2009 | Kondos et al. |
| 2009/0240328 A1 | 9/2009 | Treushnikov et al. |
| 2009/0268155 A1* | 10/2009 | Weeber .............. G02C 7/042 623/6.31 |
| 2009/0303433 A1 | 12/2009 | Shimojo |
| 2009/0309076 A1 | 12/2009 | He et al. |
| 2009/0323011 A1 | 12/2009 | He et al. |
| 2009/0323012 A1 | 12/2009 | He et al. |
| 2010/0016962 A1 | 1/2010 | Hong et al. |
| 2010/0035067 A1 | 2/2010 | Colton |
| 2010/0039612 A1 | 2/2010 | Levinson et al. |
| 2010/0065625 A1 | 3/2010 | Sabeta |
| 2010/0066973 A1 | 3/2010 | Portney |
| 2010/0076554 A1 | 3/2010 | Sandstedt et al. |
| 2010/0094262 A1 | 4/2010 | Tripathi et al. |
| 2010/0103373 A1 | 4/2010 | Hillis et al. |
| 2010/0114079 A1 | 5/2010 | Myers et al. |
| 2010/0118260 A1 | 5/2010 | Ballet et al. |
| 2010/0119735 A1 | 5/2010 | Faler et al. |
| 2010/0134754 A1* | 6/2010 | Hong .............. G02C 7/04 623/6.11 |
| 2010/0157241 A1 | 6/2010 | Kumar et al. |
| 2010/0161051 A1 | 6/2010 | Hong |
| 2010/0177279 A1 | 7/2010 | Hillis et al. |
| 2010/0188636 A1 | 7/2010 | Pinto et al. |
| 2010/0209697 A1 | 8/2010 | Bowles et al. |
| 2010/0217278 A1 | 8/2010 | Tripathi |
| 2010/0221661 A1 | 9/2010 | Bowles et al. |
| 2010/0225834 A1 | 9/2010 | Li |
| 2010/0259719 A1 | 10/2010 | Sabeta |
| 2010/0281021 A1 | 11/2010 | Weeber et al. |
| 2010/0286771 A1 | 11/2010 | Zhang et al. |
| 2010/0321635 A1 | 12/2010 | Apter et al. |
| 2011/0023924 A1 | 2/2011 | Park |
| 2011/0080628 A1 | 4/2011 | Kumar et al. |
| 2011/0112634 A1 | 5/2011 | Azar et al. |
| 2011/0128457 A1 | 6/2011 | He et al. |
| 2011/0129678 A1 | 6/2011 | He et al. |
| 2011/0135850 A1 | 6/2011 | Saha et al. |
| 2011/0140056 A1 | 6/2011 | He et al. |
| 2011/0143141 A1 | 6/2011 | He et al. |
| 2011/0157548 A1 | 6/2011 | Lesage et al. |
| 2011/0166652 A1 | 7/2011 | Bogaert et al. |
| 2011/0194069 A1 | 8/2011 | Blum et al. |
| 2011/0216273 A1 | 9/2011 | He et al. |
| 2011/0234974 A1 | 9/2011 | Lawu |
| 2011/0270389 A1 | 11/2011 | Glazer et al. |
| 2011/0279883 A1 | 11/2011 | Kumar et al. |
| 2011/0285959 A1 | 11/2011 | Gupta et al. |
| 2011/0292335 A1 | 12/2011 | Schwiegerling |
| 2012/0002141 A1 | 1/2012 | Dai et al. |
| 2012/0003401 A1 | 1/2012 | Xu et al. |
| 2012/0016350 A1 | 1/2012 | Myers et al. |
| 2012/0021144 A1 | 1/2012 | Dai et al. |
| 2012/0027960 A1 | 2/2012 | Xu et al. |
| 2012/0035724 A1 | 2/2012 | Clarke |
| 2012/0061863 A1 | 3/2012 | Cox et al. |
| 2012/0086910 A1 | 4/2012 | Kato et al. |
| 2012/0092613 A1 | 4/2012 | Azar |
| 2012/0120473 A1 | 5/2012 | Kumar et al. |
| 2012/0126185 A1 | 5/2012 | He et al. |
| 2012/0132870 A1 | 5/2012 | Xiao et al. |
| 2012/0136148 A1 | 5/2012 | Lu et al. |
| 2012/0140166 A1 | 6/2012 | Zhao |
| 2012/0140167 A1 | 6/2012 | Blum |
| 2012/0145973 A1 | 6/2012 | Bancroft et al. |
| 2012/0154740 A1 | 6/2012 | Bradley et al. |
| 2012/0156508 A1 | 6/2012 | He et al. |
| 2012/0156521 A1 | 6/2012 | He et al. |

(56) References Cited

U.S. PATENT DOCUMENTS

| | | |
|---|---|---|
| 2012/0157677 A1 | 6/2012 | He et al. |
| 2012/0176581 A1 | 7/2012 | Bradley et al. |
| 2012/0179248 A1 | 7/2012 | Azar |
| 2012/0183810 A1 | 7/2012 | Chopra |
| 2012/0200907 A1 | 8/2012 | He et al. |
| 2012/0206691 A1 | 8/2012 | Ivai |
| 2012/0212696 A1 | 8/2012 | Trajkovska et al. |
| 2012/0214992 A1 | 8/2012 | Chopra et al. |
| 2012/0224138 A1 | 9/2012 | Cohen |
| 2012/0224139 A1 | 9/2012 | Retsch, Jr. |
| 2012/0236257 A1 | 9/2012 | Hillis et al. |
| 2012/0267030 A1 | 10/2012 | Hall et al. |
| 2012/0286435 A1 | 11/2012 | Bojkova et al. |
| 2012/0320335 A1 | 12/2012 | Weeber et al. |
| 2012/0323320 A1 | 12/2012 | Simonov et al. |
| 2012/0330414 A1 | 12/2012 | McDonald |
| 2013/0004780 A1 | 1/2013 | Hervieu et al. |
| 2013/0027655 A1 | 1/2013 | Blum et al. |
| 2013/0032059 A1 | 2/2013 | Trexler et al. |
| 2013/0035760 A1 | 2/2013 | Portney |
| 2013/0050640 A1 | 2/2013 | Fiala et al. |
| 2013/0050651 A1 | 2/2013 | Azar et al. |
| 2013/0069274 A1 | 3/2013 | Zhang et al. |
| 2013/0070199 A1 | 3/2013 | Blum et al. |
| 2013/0072591 A1 | 3/2013 | Sandstedt et al. |
| 2013/0073038 A1 | 3/2013 | Azar |
| 2013/0082220 A1 | 4/2013 | Herold et al. |
| 2013/0122221 A1 | 5/2013 | Colton et al. |
| 2013/0176536 A1 | 7/2013 | Thompson et al. |
| 2013/0208347 A1 | 8/2013 | Haddock et al. |
| 2013/0211515 A1 | 8/2013 | Blum et al. |
| 2013/0211516 A1 | 8/2013 | Blum et al. |
| 2013/0215374 A1 | 8/2013 | Blum et al. |
| 2013/0218269 A1 | 8/2013 | Schachar et al. |
| 2013/0225777 A1 | 8/2013 | Hickenboth et al. |
| 2013/0228100 A1 | 9/2013 | Kleyer et al. |
| 2013/0231741 A1 | 9/2013 | Clarke |
| 2013/0245754 A1 | 9/2013 | Blum et al. |
| 2013/0261744 A1 | 10/2013 | Gupta et al. |
| 2013/0273380 A1 | 10/2013 | Hickenboth et al. |
| 2013/0274412 A1 | 10/2013 | Hickenboth et al. |
| 2013/0278891 A1 | 10/2013 | Zhao |
| 2013/0289153 A1 | 10/2013 | Sandstedt et al. |
| 2013/0308094 A1 | 11/2013 | Mohan et al. |
| 2013/0308186 A1* | 11/2013 | Cathey, Jr. .............. A61F 2/16 351/159.01 |
| 2013/0335701 A1 | 12/2013 | Canovas Vidal et al. |
| 2013/0338767 A1 | 12/2013 | Mazzocchi et al. |
| 2014/0043672 A1 | 2/2014 | Clarke et al. |
| 2014/0055744 A1 | 2/2014 | Wildsmith et al. |
| 2014/0066537 A1 | 3/2014 | Jerome et al. |
| 2014/0078583 A1 | 3/2014 | DeMeio et al. |
| 2014/0080972 A1 | 3/2014 | Slezak et al. |
| 2014/0107777 A1 | 4/2014 | Portney |
| 2014/0118683 A1 | 5/2014 | Jubin et al. |
| 2014/0125949 A1 | 5/2014 | Shea et al. |
| 2014/0125954 A1 | 5/2014 | Kingston et al. |
| 2014/0148899 A1 | 5/2014 | Fehr et al. |
| 2014/0152953 A1 | 6/2014 | Guillon et al. |
| 2014/0154514 A1 | 6/2014 | He et al. |
| 2014/0155572 A1 | 6/2014 | Bojkova |
| 2014/0166948 A1 | 6/2014 | He et al. |
| 2014/0171612 A1 | 6/2014 | Bojkova et al. |
| 2014/0178513 A1 | 6/2014 | Matthews |
| 2014/0199521 A1 | 7/2014 | Carpenter |
| 2014/0232982 A1 | 8/2014 | Iwai |
| 2014/0240657 A1 | 8/2014 | Pugh et al. |
| 2014/0243972 A1 | 8/2014 | Wanders |
| 2014/0256935 A1 | 9/2014 | Dabideen et al. |
| 2014/0264979 A1 | 9/2014 | Park et al. |
| 2014/0265010 A1 | 9/2014 | Park et al. |
| 2014/0272111 A1 | 9/2014 | Bradford et al. |
| 2014/0272468 A1 | 9/2014 | DeMeio et al. |
| 2014/0277051 A1 | 9/2014 | Schachar et al. |
| 2014/0277437 A1 | 9/2014 | Currie |
| 2014/0327875 A1 | 11/2014 | Blum et al. |
| 2014/0340632 A1 | 11/2014 | Pugh et al. |
| 2014/0347624 A1 | 11/2014 | Ando et al. |
| 2014/0350672 A1 | 11/2014 | Hong |
| 2015/0005877 A1 | 1/2015 | Wanders |
| 2015/0022775 A1 | 1/2015 | Ando et al. |
| 2015/0029460 A1 | 1/2015 | Bradley et al. |
| 2015/0044446 A1 | 2/2015 | Trexler et al. |
| 2015/0057748 A1 | 2/2015 | Azar |
| 2015/0088253 A1 | 3/2015 | Doll et al. |
| 2015/0131056 A1 | 5/2015 | Paille et al. |
| 2015/0133901 A1 | 5/2015 | Serdarevic et al. |
| 2015/0138492 A1 | 5/2015 | Kumar et al. |
| 2015/0141661 A1 | 5/2015 | He et al. |
| 2015/0141662 A1 | 5/2015 | He et al. |
| 2015/0141663 A1 | 5/2015 | He et al. |
| 2015/0152271 A1 | 6/2015 | Bradford et al. |
| 2015/0159022 A1 | 6/2015 | Bradford et al. |
| 2015/0182331 A1 | 7/2015 | Blum et al. |
| 2015/0230979 A1 | 8/2015 | Serdarevic et al. |
| 2015/0230985 A1 | 8/2015 | Serdarevic et al. |
| 2015/0274910 A1 | 10/2015 | Kumar et al. |
| 2015/0331253 A1 | 11/2015 | Choi et al. |
| 2015/0342727 A1 | 12/2015 | Fernandez Gutierrez et al. |
| 2015/0362748 A1 | 12/2015 | Pugh et al. |
| 2015/0368408 A1 | 12/2015 | Trexler et al. |
| 2015/0378180 A1 | 12/2015 | Blum et al. |
| 2016/0051360 A1 | 2/2016 | Tripathi |
| 2016/0060205 A1 | 3/2016 | He et al. |
| 2016/0062143 A1 | 3/2016 | Brennan et al. |
| 2016/0062145 A1 | 3/2016 | Brennan et al. |
| 2016/0085089 A1 | 3/2016 | Hillis et al. |
| 2016/0100938 A1 | 4/2016 | Bogaert et al. |
| 2016/0113727 A1 | 4/2016 | Tripathi et al. |
| 2016/0185910 A1 | 6/2016 | Bojkova |
| 2016/0209561 A1 | 7/2016 | DeMeio et al. |
| 2016/0216535 A1 | 7/2016 | Zhao |
| 2016/0220350 A1 | 8/2016 | Gerlach |
| 2016/0220352 A1 | 8/2016 | Choi et al. |
| 2016/0238758 A1 | 8/2016 | Turpen et al. |
| 2016/0243579 A1 | 8/2016 | Koenig, II et al. |
| 2016/0245967 A1 | 8/2016 | Koenig, II et al. |
| 2016/0279886 A1 | 9/2016 | Lynch et al. |
| 2016/0288157 A1 | 10/2016 | Lynch et al. |
| 2016/0296110 A1 | 10/2016 | Dorronsoro et al. |
| 2016/0299265 A1 | 10/2016 | Ghatak et al. |
| 2016/0302915 A1 | 10/2016 | Sayegh |
| 2016/0324628 A1 | 11/2016 | Gupta et al. |
| 2016/0324629 A1 | 11/2016 | Sandstedt et al. |
| 2016/0332995 A1 | 11/2016 | He et al. |
| 2016/0333262 A1 | 11/2016 | He et al. |
| 2016/0341978 A1 | 11/2016 | Schwiegerling |
| 2016/0363698 A1 | 12/2016 | Fan et al. |
| 2016/0377887 A1 | 12/2016 | Waite et al. |
| 2017/0002174 A1 | 1/2017 | Bhagwagar et al. |
| 2017/0009014 A1 | 1/2017 | Bhagwagar et al. |
| 2017/0035609 A1 | 2/2017 | Schachar et al. |
| 2017/0037173 A1 | 2/2017 | Saha et al. |
| 2017/0042665 A1 | 2/2017 | Currie et al. |
| 2017/0075140 A1 | 3/2017 | Hillis et al. |
| 2017/0105835 A1 | 4/2017 | Neuhann et al. |
| 2017/0123231 A1 | 5/2017 | Franklin et al. |
| 2017/0131570 A1 | 5/2017 | Thompson |
| 2017/0131571 A1 | 5/2017 | Waite et al. |
| 2017/0139230 A1 | 5/2017 | Ambler et al. |
| 2017/0146820 A1 | 5/2017 | Brennan et al. |
| 2017/0146822 A1 | 5/2017 | Wildsmith et al. |
| 2017/0153359 A1 | 6/2017 | Bojkova et al. |
| 2017/0209259 A1 | 7/2017 | Choi et al. |
| 2017/0213306 A9 | 7/2017 | Weeber et al. |
| 2017/0219846 A1 | 8/2017 | Ando |
| 2017/0224474 A1 | 8/2017 | Piers et al. |
| 2017/0227789 A1 | 8/2017 | Ando et al. |
| 2017/0235022 A1 | 8/2017 | Bojkova et al. |
| 2017/0239038 A1 | 8/2017 | Choi et al. |
| 2017/0252151 A1 | 9/2017 | Mackool |
| 2017/0258576 A1 | 9/2017 | Ghabra et al. |
| 2017/0261768 A1 | 9/2017 | Ambler et al. |
| 2017/0273778 A1 | 9/2017 | Zhao |

(56) References Cited

U.S. PATENT DOCUMENTS

| | | |
|---|---|---|
| 2017/0273779 A1 | 9/2017 | Zhao |
| 2017/0273780 A1 | 9/2017 | Zhao |
| 2017/0273781 A1 | 9/2017 | Zhao |
| 2017/0275534 A1 | 9/2017 | Reddy et al. |
| 2017/0276962 A1 | 9/2017 | Zhao |
| 2017/0290502 A1 | 10/2017 | Linder et al. |
| 2017/0290657 A1 | 10/2017 | Luque |
| 2017/0325937 A1 | 11/2017 | Weeber et al. |
| 2018/0015678 A1 | 1/2018 | Damodharan et al. |
| 2018/0024377 A1 | 1/2018 | Kumar et al. |
| 2018/0051037 A1 | 2/2018 | Deng et al. |
| 2018/0056615 A1 | 3/2018 | Turpen et al. |
| 2018/0086725 A1 | 3/2018 | Kumar et al. |
| 2018/0092739 A1 | 4/2018 | Pagnoulle et al. |
| 2018/0095190 A1 | 4/2018 | Frease et al. |
| 2018/0098694 A1 | 4/2018 | Schmeder |
| 2018/0125710 A1 | 5/2018 | Schachar et al. |
| 2018/0127653 A1 | 5/2018 | Kumar et al. |
| 2018/0147050 A1 | 5/2018 | Choi et al. |
| 2018/0147052 A1 | 5/2018 | Hong et al. |
| 2018/0164608 A1 | 6/2018 | Schmeder et al. |
| 2018/0171154 A1 | 6/2018 | Lu et al. |
| 2018/0180902 A1 | 6/2018 | Franklin et al. |
| 2018/0196284 A1 | 7/2018 | Schmeder et al. |
| 2018/0210330 A1 | 7/2018 | Tomasulo et al. |
| 2018/0243082 A1 | 8/2018 | Zheleznyak et al. |
| 2018/0249151 A1 | 8/2018 | Freeman et al. |
| 2018/0256317 A1 | 9/2018 | Bogaert et al. |
| 2018/0271741 A1 | 9/2018 | Dorronsoro et al. |
| 2018/0275428 A1 | 9/2018 | Ando |
| 2018/0289469 A1 | 10/2018 | Lux et al. |
| 2018/0290408 A1 | 10/2018 | Park et al. |
| 2018/0291007 A1 | 10/2018 | He et al. |
| 2018/0291008 A1 | 10/2018 | He et al. |
| 2018/0291009 A1 | 10/2018 | He et al. |
| 2018/0296324 A1 | 10/2018 | Zhang |
| 2018/0299599 A1 | 10/2018 | Kumar et al. |
| 2018/0299600 A1 | 10/2018 | Miller et al. |
| 2018/0303601 A1 | 10/2018 | Lux et al. |
| 2018/0311034 A1 | 11/2018 | Hong et al. |
| 2018/0321510 A1 | 11/2018 | Vetro |
| 2018/0329228 A1 | 11/2018 | Brennan et al. |
| 2018/0329229 A1 | 11/2018 | Brennan et al. |
| 2018/0329234 A1 | 11/2018 | Blum et al. |
| 2018/0344452 A1 | 12/2018 | Liao et al. |
| 2018/0348524 A1 | 12/2018 | Blum et al. |
| 2018/0348529 A1 | 12/2018 | Blum et al. |
| 2018/0368972 A1 | 12/2018 | Rosen et al. |
| 2019/0004221 A1 | 1/2019 | Weeber et al. |
| 2019/0004331 A1 | 1/2019 | Weeber et al. |
| 2019/0029808 A1 | 1/2019 | Piers et al. |
| 2019/0041664 A1 | 2/2019 | Ando |
| 2019/0047967 A1 | 2/2019 | Fromentin et al. |
| 2019/0053893 A1 | 2/2019 | Currie et al. |
| 2019/0107647 A1 | 4/2019 | Fromentin |
| 2019/0125523 A1 | 5/2019 | Barzilay |
| 2019/0133755 A1 | 5/2019 | Goldshleger et al. |
| 2019/0142576 A1 | 5/2019 | Goldshleger et al. |
| 2019/0142577 A1 | 5/2019 | Xie |
| 2019/0169438 A1 | 6/2019 | Fromentin et al. |
| 2019/0212473 A1 | 7/2019 | Fromentin et al. |
| 2019/0224000 A1 | 7/2019 | Choi et al. |
| 2019/0224001 A1 | 7/2019 | Choi et al. |
| 2019/0224803 A1 | 7/2019 | Masad et al. |
| 2019/0231518 A1 | 8/2019 | Sarver et al. |
| 2019/0247181 A1 | 8/2019 | Peyman |
| 2019/0254810 A1 | 8/2019 | Tiwari et al. |
| 2019/0290423 A1 | 9/2019 | Sayegh |
| 2019/0291128 A1 | 9/2019 | Zezinka et al. |
| 2019/0307556 A1 | 10/2019 | Sarver et al. |
| 2019/0307557 A1 | 10/2019 | De Carvalho et al. |
| 2019/0314148 A1 | 10/2019 | Lui |
| 2019/0321163 A1 | 10/2019 | Clamen et al. |
| 2019/0339545 A1 | 11/2019 | Schwiegerling |
| 2019/0343682 A1 | 11/2019 | Schachar et al. |
| 2019/0343683 A1 | 11/2019 | Zheleznyak et al. |
| 2019/0345286 A1 | 11/2019 | Valeri et al. |
| 2019/0353925 A1 | 11/2019 | Biskop et al. |
| 2019/0358027 A1 | 11/2019 | Hong et al. |
| 2019/0358919 A1 | 11/2019 | Kumar et al. |
| 2019/0361269 A1 | 11/2019 | Waite et al. |
| 2019/0365528 A1 | 12/2019 | Choi et al. |
| 2019/0374334 A1 | 12/2019 | Brady et al. |
| 2019/0375948 A1 | 12/2019 | Zheng |
| 2019/0375949 A1 | 12/2019 | Zheng et al. |
| 2019/0385342 A1 | 12/2019 | Freeman et al. |
| 2020/0009605 A1 | 1/2020 | Kumar et al. |
| 2020/0012110 A1 | 1/2020 | Blum et al. |
| 2020/0022840 A1 | 1/2020 | Kahook et al. |
| 2020/0030081 A1 | 1/2020 | Lux et al. |
| 2020/0033666 A1 | 1/2020 | Li |
| 2020/0048216 A1 | 2/2020 | Kumar et al. |
| 2020/0085569 A1 | 3/2020 | Kaschke et al. |
| 2020/0103571 A1 | 4/2020 | He et al. |
| 2020/0113736 A1 | 4/2020 | Bos et al. |
| 2020/0121450 A1 | 4/2020 | Sarver et al. |
| 2020/0122487 A1 | 4/2020 | Rodriguez et al. |
| 2020/0172798 A1 | 6/2020 | Stayshich et al. |
| 2020/0209649 A1 | 7/2020 | Holmstrom et al. |
| 2020/0218089 A1 | 7/2020 | Dubail et al. |
| 2020/0218093 A1 | 7/2020 | Blum et al. |
| 2020/0253722 A1 | 8/2020 | Choi et al. |
| 2020/0268506 A1 | 8/2020 | Zhao |
| 2020/0271958 A1 | 8/2020 | Zhao |
| 2020/0285075 A1 | 9/2020 | Zhao |
| 2020/0292847 A1 | 9/2020 | Wildsmith et al. |
| 2020/0292849 A1 | 9/2020 | Schmeder et al. |
| 2020/0326562 A1 | 10/2020 | Zhao |
| 2020/0333632 A1 | 10/2020 | Franklin et al. |
| 2020/0386913 A1 | 12/2020 | Fromentin et al. |
| 2020/0391457 A1 | 12/2020 | Damodharan et al. |
| 2020/0409178 A1 | 12/2020 | Zhao |
| 2021/0002415 A1 | 1/2021 | Zheng et al. |
| 2021/0003863 A1 | 1/2021 | Schwiegerling |
| 2021/0030532 A1 | 2/2021 | Hong et al. |
| 2021/0052368 A1 | 2/2021 | Smadja et al. |
| 2021/0055217 A1 | 2/2021 | Blackburn et al. |
| 2021/0059812 A1 | 3/2021 | Kontur et al. |
| 2021/0077251 A1 | 3/2021 | Barzilay |
| 2021/0079009 A1 | 3/2021 | Walters et al. |
| 2021/0080755 A1 | 3/2021 | Balasubramanian et al. |
| 2021/0116604 A1 | 4/2021 | Fromentin et al. |
| 2021/0169640 A1 | 6/2021 | Kaschke et al. |
| 2021/0177576 A1 | 6/2021 | Zheleznyak et al. |
| 2021/0177577 A1 | 6/2021 | Zheleznyak et al. |
| 2021/0177578 A1 | 6/2021 | Zheleznyak et al. |
| 2021/0177579 A1 | 6/2021 | Zheleznyak et al. |
| 2021/0196520 A1 | 7/2021 | Zheleznyak et al. |
| 2021/0220118 A1 | 7/2021 | Choi et al. |
| 2021/0228335 A1 | 7/2021 | Hong et al. |
| 2021/0228337 A1 | 7/2021 | Sarver et al. |
| 2021/0228338 A1 | 7/2021 | Choi et al. |
| 2021/0247626 A1 | 8/2021 | Zakharov et al. |
| 2021/0251718 A1 | 8/2021 | Tripathi |
| 2021/0298893 A1 | 9/2021 | Sarver et al. |
| 2021/0318556 A1 | 10/2021 | Shimojo et al. |
| 2021/0341760 A1 | 11/2021 | Burgos et al. |

FOREIGN PATENT DOCUMENTS

| | | |
|---|---|---|
| AU | 2008200665 B2 | 3/2008 |
| AU | 2011218693 B2 | 9/2011 |
| AU | 2012100457 A4 | 5/2012 |
| AU | 2012201991 B2 | 5/2012 |
| AU | 2013200699 B2 | 2/2013 |
| AU | 2013200702 B2 | 2/2013 |
| AU | 2013202083 B2 | 4/2013 |
| AU | 2015201867 A1 | 4/2013 |
| AU | 2017228616 B2 | 4/2018 |
| BR | 102016011774-7 A2 | 12/2017 |
| CA | 1275553 C | 10/1990 |
| CA | 2037556 A1 | 9/1991 |
| CA | 2388766 A1 | 12/2003 |
| CA | 2678025 A1 | 8/2009 |

(56) References Cited

FOREIGN PATENT DOCUMENTS

| | | |
|---|---|---|
| CA | 2824656 A1 | 7/2012 |
| CN | 1021990 C | 9/1993 |
| CN | 100543518 C | 9/2009 |
| CN | 108066046 B | 11/2019 |
| CN | 209808722 U | 12/2019 |
| CN | 209992764 | 1/2020 |
| CN | 209992764 U | 1/2020 |
| CZ | 280372 B6 | 1/1996 |
| DE | 3924838 A1 | 7/1989 |
| DE | 29924922 U1 | 9/2006 |
| DE | 202016105180 U1 | 10/2017 |
| DE | 202016105181 U1 | 10/2017 |
| DE | 20 2019 000 174 U1 | 4/2019 |
| EP | 1063556 B1 | 3/2006 |
| EP | 2363426 A1 | 9/2011 |
| EP | 2548533 A1 | 10/2013 |
| EP | 3375410 A1 | 9/2018 |
| EP | 3415118 A1 | 12/2018 |
| EP | 3461460 | 4/2019 |
| ES | 2208077 B2 | 5/2005 |
| ES | 2277705 B2 | 7/2008 |
| GB | 2038020 B | 7/1980 |
| GB | 2105866 A | 3/1983 |
| JP | 3814017 B2 | 5/1996 |
| JP | 3347514 B2 | 11/2002 |
| KR | 0133917 B1 | 4/1998 |
| KR | 10-1754196 B1 | 7/2017 |
| NL | 2008054 C2 | 12/2011 |
| RU | 2002456 C1 | 11/1993 |
| RU | 2012136016 A | 2/2014 |
| RU | 2682481 C1 | 3/2019 |
| TW | I475278 B | 3/2015 |
| UA | 691733 B2 | 2/1992 |
| WO | WO-9634365 A1 | 10/1996 |
| WO | WO-9805279 A1 | 2/1998 |
| WO | WO-9956671 A1 | 11/1999 |
| WO | WO-0072051 A2 | 11/2000 |
| WO | WO-02085245 A2 | 10/2002 |
| WO | WO-2005006034 A2 | 1/2005 |
| WO | WO-2006124016 A1 | 11/2006 |
| WO | WO-2017006113 A1 | 1/2007 |
| WO | WO-2007146265 A2 | 12/2007 |
| WO | WO-2009076670 A1 | 6/2009 |
| WO | WO-2011059430 A1 | 5/2011 |
| WO | WO-2011060047 A1 | 5/2011 |
| WO | WO-2011080730 A1 | 7/2011 |
| WO | WO-2011107723 A1 | 9/2011 |
| WO | WO-2011163668 A2 | 12/2011 |
| WO | WO-2012083143 A1 | 6/2012 |
| WO | WO-2012138426 A2 | 10/2012 |
| WO | WO-2012167284 A1 | 12/2012 |
| WO | WO-2012170066 A1 | 12/2012 |
| WO | WO-2012170287 A1 | 12/2012 |
| WO | WO-2013163532 A1 | 10/2013 |
| WO | WO-2014120607 A1 | 1/2014 |
| WO | WO-2014058315 A1 | 4/2014 |
| WO | WO-2014065659 A1 | 5/2014 |
| WO | WO-2014120601 A1 | 8/2014 |
| WO | WO-2014140905 A1 | 9/2014 |
| WO | WO-2014151543 A1 | 9/2014 |
| WO | WO-2014152259 A1 | 9/2014 |
| WO | WO 2015-008502 | 6/2015 |
| WO | WO-2015142559 A1 | 9/2015 |
| WO | WO-2015142561 A1 | 9/2015 |
| WO | WO-2015142562 A1 | 9/2015 |
| WO | WO-2015159374 A1 | 10/2015 |
| WO | WO-2018041098 A1 | 3/2018 |
| WO | WO-2018167099 A2 | 9/2018 |
| WO | WO-2018200717 A1 | 11/2018 |
| WO | WO-2018219671 A1 | 12/2018 |
| WO | WO-2018223150 A1 | 12/2018 |
| WO | WO-2019001724 A1 | 1/2019 |
| WO | WO-2019010874 A1 | 1/2019 |
| WO | WO-2019219334 A1 | 4/2019 |
| WO | WO-2019106031 A1 | 6/2019 |
| WO | WO-2019129348 A1 | 7/2019 |
| WO | WO-2019130030 A1 | 7/2019 |
| WO | WO-2019130031 A1 | 7/2019 |
| WO | WO-2019138411 A1 | 7/2019 |
| WO | WO-2019173836 A1 | 9/2019 |
| WO | 2020/011250 A1 | 1/2020 |
| WO | WO-2020053864 A1 | 3/2020 |

OTHER PUBLICATIONS

English Abstract of AU 2011204781-B2 published on Feb. 2, 2012.
English Abstract of CA-3024244-A1 published on Sep. 10, 2019.
English Abstract of CA-2717328-C published on Apr. 14, 2012.
English Abstract of CN-209808722-U published on Dec. 20, 2019.
English Abstract of ES-2277705-B2 published on Jul. 16, 2007.
English Abstract of JP-3814017-B2 published on May 31, 1996.
Garrard et al. (2008). "Design, Fabrication and Testing of Kinoform Lenses," Proceedings of the ASPE 44: pp. 558-561.
International Search Report and Written Opinion mailed Aug. 16, 2021, directed to International Application No. PCT/IB2021/054657; 11 pages.
Moreno et al. (Jun. 1997). "High efficiency diffractive lenses: Deduction of kinoform profile," Am. J. Phys. 65(6): 556-562.
Riedl. "Diamond-turned diffractive optical elements for the infrared: suggestion for specification standardization and manufacturing remarks," SPIE's 2020 International Symposium on Optical Science, Engineering, and Instrumentation, May 28, 2020, San Diego, California; pp. 257-268.

\* cited by examiner

DOUBLE-SIDED ASPHERIC DIFFRACTIVE MULTIFOCAL LENS, MANUFACTURE, AND USES THEREOF

CROSS-REFERENCE TO RELATED APPLICATIONS

The application claims benefit of priority under 35 U.S.C. § 119(e) of U.S. Ser. No. 63/032,892, filed Jun. 1, 2020, the entire content of which is incorporated by reference in its entirety.

FIELD

The present disclosure relates generally to ophthalmic lenses, and more specifically to a novel double-sided aspheric diffractive multifocal lens, design, manufacture, and uses thereof.

BACKGROUND

Ophthalmology is the field of medicine directed to the anatomy, physiology and diseases of the human eye. The anatomy of the human eye is rather complex. The main structures of the eye include the cornea, a spherical clear tissue at the outer front of the eye; the iris, which is the colored part of the eye; the pupil, an adaptable aperture in the iris that regulates the amount of light received in the eye; the crystalline lens, a small clear disk inside the eye that focuses light rays onto the retina; the retina is a layer that forms the rear or backside of the eye and transforms sensed light into electrical impulses that travel through the optic nerve to the brain. The posterior chamber, i.e., the space between the retina and the lens, is filled with aqueous humour, and the anterior chamber, i.e., the space between the lens and the cornea, is filled with vitreous humour a clear, jelly-like substance.

The natural crystalline lens has a flexible, transparent, biconvex structure, and together with the cornea, operates to refract light to be focused on the retina. The lens is flatter on its anterior side than on its posterior side and its curvature is controlled by the ciliary muscles to which the lens connects by suspensory ligaments, called zonules. By changing the curvature of the lens, the focal distance of the eye is changed so as to focus on objects at various distances. To view an object at a short distance from the eye, the ciliary muscles contract, and the lens thickens, resulting in a rounder shape and thus high refractive power. Changing focus to an object at a greater distance requires the relaxation of the lens and thus increasing the focal distance. This process of changing curvature and adapting the focal distance of the eye to form a sharp image of an object at the retina is called accommodation.

In humans, the refractive power of the crystalline lens in its natural environment is approximately 18-20 diopters, roughly one-third of the total optical power of the eye. The cornea provides the remaining 40 diopters of the total optical power of the eye.

With the ageing of the eye, the opaqueness of the lens diminishes, called a cataract. Some diseases like diabetes, trauma, some medications, and excessive UV light exposure may also cause a cataract. A cataract is painless and results in a cloudy, blurry vision. Treatments for cataracts include surgery, by which the cloudy lens is removed and replaced with an artificial one, generally called an intraocular lens (IOL or IOLs).

Another age-related effect is called presbyopia, which is manifested by difficulty in reading small print or seeing nearby pictures clearly. Presbyopia generally is believed to be caused by a thickening and loss of flexibility of the natural lens inside the eye. Age-related changes also take place in the ciliary muscles surrounding the lens. With less elasticity it becomes harder to focus at objects close to the eye.

A variety of intraocular lenses are also employed for correcting other visual disorders, such as myopia or near-sightedness, when the eye is unable to see distant objects caused by the cornea having too much curvature, for example. The effect of myopia is that distant light rays focus at a point in front of the retina, rather than directly on its surface. Hyperopia or farsightedness, caused by an abnormally flat cornea, such that light rays entering the eye focus behind the retina, not allowing to focus on objects that are close, and astigmatism, which is another common cause of visual difficulty in which images are blurred due to an irregularly shaped cornea.

In the majority of cases, intraocular lenses are implanted in a patient's eye during cataract surgery, to replace the natural crystalline lens and compensate for the loss of optical power of the removed lens. Modern IOL optics are designed to have a multifocal optic for providing short, intermediary and distance vision of objects, also called multifocal IOL, or more specific trifocal lenses. Presbyopia is corrected by eyeglasses or contact lenses and patient's may also opt for multifocal optics. In some cases, an IOL can include diffractive structures to have not only a far-focus power but also a near-focus power, thereby providing a degree of pseudo-accommodation. However, a variety of aberrations, such as spherical and astigmatic aberrations, can adversely affect the optical performance of such lenses. For example, spherical aberrations can degrade vision contrast, especially for large pupil sizes.

Accordingly, what is needed is intraocular lenses that can simultaneously provide a near focus, an intermediate focus, and a distance focus, which can also address adverse effects such as spherical and astigmatic aberrations, thereby providing enhanced contrast and improved visual acuity.

SUMMARY

The present disclosure is related to a double-sided aspheric diffractive multifocal lens, which can eliminate spherical and astigmatic aberrations and provide enhanced contrast and improved visual acuity. In some embodiments, the diffractive multifocal lens can include a lens body, the lens body can include: a first aspheric surface; and a second aspheric surface including a central zone and a plurality of diffractive elements comprising concentric annular zones extending in a radial direction, each concentric annular zone having a periodically structured curve comprising two smooth turning points between two sharp turning points, thereby producing a near focus ($f_2$), an intermediate focus ($f_1$), and a distance focus ($f_0$).

In some embodiments, the first aspheric surface is anterior surface, and the second aspheric surface is posterior surface. In some embodiments, the first aspheric surface can include a toric component. In some embodiments, a height profile of the first aspheric surface and/or the second aspheric surface is represented by:

$$Z_{asp}(r) = \frac{cr^2}{1 + \sqrt{1 - (1+k)c^2 r^2}} + \sum_{i=2}^{n} A_i r^{2i}$$

wherein $Z_{asp}$ is the height profile of the aspheric structure, r is the radial distance in millimeters, c is the curvature, k is the conic constant, and $A_i$ is high order aspheric coefficients.

In some embodiments, a height profile of the diffractive elements is represented by:

$$Z_{diff}(r) = \Phi_{(n)}(r) \times \frac{\lambda}{n_1 - n_0}$$

wherein $\lambda$ is the design wavelength, $\Phi_{(n)}(r)$ is phase profile, $n_1$ is refractive index of lens material, and $n_0$ is refractive index of a medium covering the lens.

In some embodiments, phase profile $\Phi_{(n)}(r)$ can be represented as:

$$\Phi_{(n)}(r) = A \times \sin\left(\left(B \times \frac{r - r_n}{r_{n+1} - r_n} + C\right) \times \pi\right) + D$$

wherein r is the radial distance of the lens in millimeter, $r_n$ is radius of $n^{th}$ zone, $r_{n+1}$ is radius of $(n+1)^{th}$ zone, and A, B, C and D, are light distribution parameters. A is amplitude; B is the period as $$\frac{2\pi}{B};$$

C is phase shift; D is vertical shift.

In some embodiments, phase profile $\Phi_{(n)}(r)$ can be in the range of $-4\pi \leq \Phi_{(n)}(r) \leq 4\pi$. In some embodiments, the distance focus ($f_0$), the intermediate focus ($f_1$), and the near focus ($f_2$) are in the range of:

$$0D \leq \frac{1}{f_0} \leq 55D, 1D \leq \frac{1}{f_1} - \frac{1}{f_0} \leq 2.5D, 2D \leq \frac{1}{f_2} - \frac{1}{f_0} \leq 5D.$$

In some embodiments, the diffractive multifocal lens can be an intraocular lens (IOL). In some embodiments, the diffractive multifocal lens can further include a pair of haptics extended outwardly from the lens body. In some embodiments, the IOL is a posterior chamber IOL, and the posterior chamber IOL is configured to be implanted into capsular bag of a human eye.

In some embodiments, the present disclosure is directed to a method of treating an ophthalmic disease or disorder in a subject, the method can include implanting into an eye of the subject a diffractive multifocal lens comprising a lens body, the lens body can include a first aspheric surface; and a second aspheric surface comprising a central zone and a plurality of diffractive elements comprising concentric annular zones extending in a radial direction, each concentric annular zone having a periodically structured curve comprising two smooth turning points between two sharp turning points.

In some embodiments, the present disclosure is directed to a method of manufacturing a diffractive multifocal lens, the method can include (a) manufacturing a first aspheric surface optionally comprising a toric component; (b) manufacturing a second aspheric surface; and (c) generating a central zone and diffractive elements comprising a plurality of concentric annular zones on the second aspheric surface, each concentric annular zone having a periodically structured curve comprising two smooth turning points between two sharp turning points, thereby producing a near focus ($f_2$), an intermediate focus ($f_1$), and a distance focus ($f_0$). In some embodiment, the method can further include performing an in situ image quality analysis to ensure the performance meets the pre-established quality criteria.

DETAILED DESCRIPTION

Figure 1A:
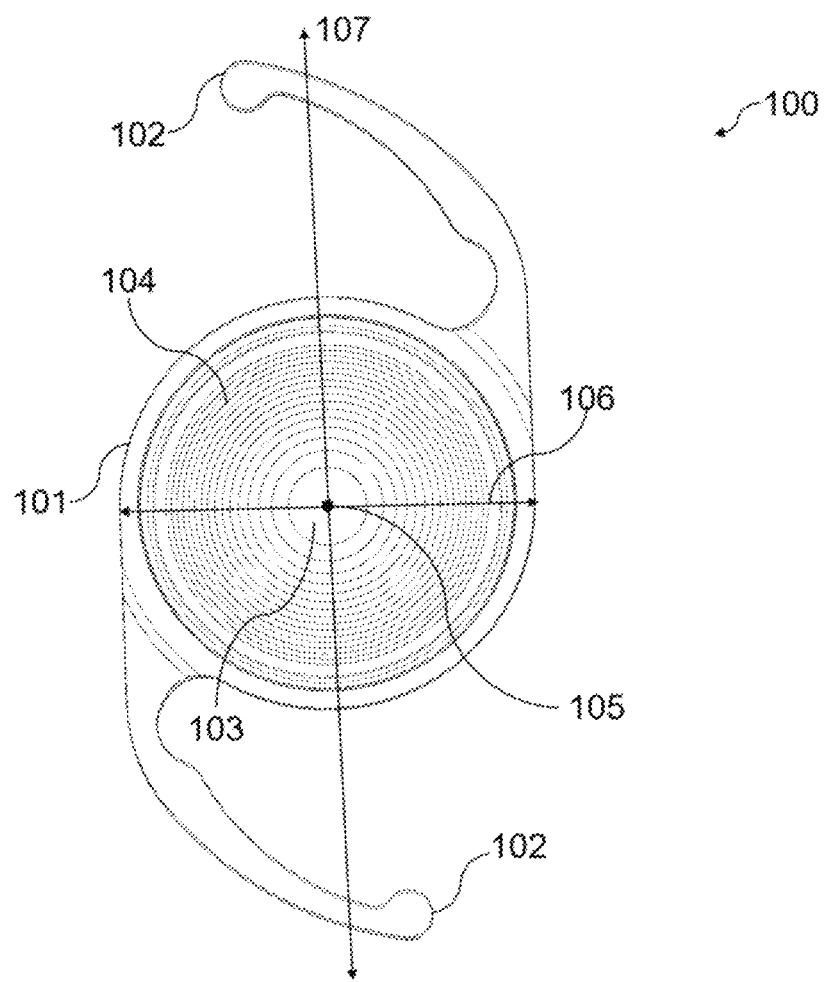
FIG. 1A illustrates the top view of a double-sided aspheric multifocal diffractive IOL, according to some embodiments of the present disclosure.

The present disclosure is related to a double-sided aspheric diffractive multifocal lens and methods of designing and manufacturing of such lenses in the field of ophthalmology. The lens can include an aspheric anterior surface and an aspheric posterior surface. One of the two surfaces can include a plurality of concentric diffractive multifocal zones. The other surface can optionally include a toric component. The double-sided aspheric surface design results in an improvement of the modulation transfer function (MTF) of the lens-eye combination by aberration reduction and vision contrast enhancement as compared to one-sided aspheric lens. The surface having a plurality of concentric diffractive multifocal zones can produce a near focus, an intermediate focus, and a distance focus.

Multifocal IOLs are commonly used to treat presbyopia, a condition in which the eye exhibits a progressively diminished ability to focus on near objects. Human beings become presbyopic due to aging, and the effect typically becomes noticeable starting at about the age of 40-45 years old, when they discover they need reading glasses. Presbyopic individuals who wear corrective lenses may then find that they need two separate prescriptions, preferably within the same bifocal lens, one for reading (near) and another for driving (distance). A trifocal lens can further improve vision at intermediate distances, for example, when working at a computer.

Diffractive IOLs can have a repeating structure that may be formed in the surface of an optical element by a fabrication method such as, for example, cutting the surface using a lathe that may be equipped with a cutting head made of a hard mineral such as diamond or sapphire; direct write patterning using a high energy beam such as a laser beam or electron beam or a similar method of ablating the surface; etching the surface using a photolithographic patterning process; or molding the surface. The diffractive structure is typically a series of concentric annular zones, which requires each zone to become progressively narrower from the center to the edge of the lens. There may be, for example, about 5 to 30 zones between the center and the edge of the lens. The surface profile within each zone is typically a smoothly varying function such as an arc, a parabola, or a line. At the outer periphery of each zone there is a discrete step in the vertical surface profile. The resulting surface structure can act as a circularly symmetric diffraction grating that disperses light into multiple diffraction orders, each diffraction order having a consecutive number, zero, one, two, three and so forth.

Diffractive IOLs lenses may be used for correcting presbyopia. In such an application, the lens can include one refractive surface and one diffractive surface. In practice, the light energy passing through a diffractive lens is typically concentrated into one, two, or three diffractive orders, while contributing an insignificant amount of light energy to other diffractive orders.

Existing designs for multifocal IOLs use either refractive optics, a combination refractive/diffractive design, or diffractive lenses that direct light into a single diffractive order. However, the fabrication of such IOLs can be time-consuming and expensive. Therefore, there is a need for improved ophthalmic lenses, particularly for improved diffractive IOLs that can be more readily fabricated.

Figure 1B:
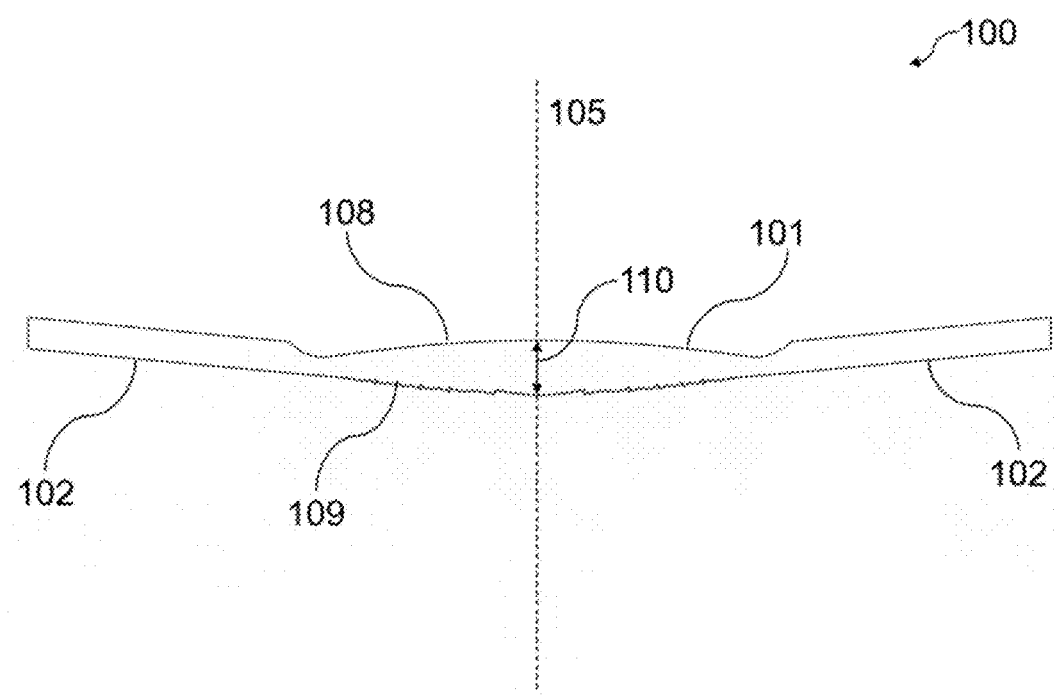
FIG. 1B shows the cross-sectional view of a double-sided aspheric multifocal diffractive IOL, according to some embodiments of the present disclosure.

The present disclosure is directed to an intraocular lens (IOL), which provides an extended vision range. FIG. 1A shows a top view of a double-sided aspheric multifocal diffractive IOL 100, according to some embodiments of the present disclosure. FIG. 1B shows a cross-sectional view of the double-sided aspheric multifocal diffractive IOL 100, according to some embodiments of the present disclosure. IOL 100 can include a light transmissive circular disk-shaped lens body 101 with an optic diameter of 106 and a center thickness 110, as well as a pair of haptics 102 as flexible support for the IOL when implanted into patient's eye, with a total outer diameter 107. Lens body 101 can include an anterior surface 108, a posterior surface 109, a central zone 103 and a plurality of diffraction elements 104 on the posterior surface 109. Lens body 101 can include an optical axis 105 extending transverse to the anterior surface 108 and posterior surface 109. A skilled artisan in the art will appreciate that the optical axis 105 is a virtual axis for purposes of referring to the optical properties of IOL 100. The pair of haptics 102 can be extended outwardly from the lens body 101 for supporting the IOL 100 after being implanted in the human eye. In some embodiments, the haptics 102 of IOL 100 can hold the IOL in place in the capsular bag.

In some embodiments, lens body 101 can take the shape of biconvex shape. Other shapes of lens body 101 can include, but are not limited to, plano-convex, biconcave, plano-concave shape, or combinations of convex and concave shapes. In some embodiments, both anterior surface 108 and posterior surface 109 can feature an aspheric structure, providing a double-sided asphericity for IOL 100.

Diffractive element 104 can include diffractive rings or steps or also known as diffractive zones having a characteristic radial separation to produce constructive interference at characteristic foci on the optic area of the IOL. In some embodiments, diffractive elements 104 can include about 3 to about 30 diffractive rings/zones. In some embodiments, diffractive elements 104 can include about 5, 10, 15, 20, or 25 diffractive rings/zones. The IOL can contain diffractive elements on one of the surfaces or both surfaces of the lens. In some embodiments, the diffractive elements 104 can be placed on the posterior surface of the IOL. In some embodiments, the diffractive elements can be placed at the posterior surface, because there is less light scattering effect at the posterior surface than at the anterior surface. The plurality of diffractive elements 104 can include rings or zones extending concentrically with respect to the optical axis 105 through the central zone 103 over at least part of the posterior surface 109 of the lens body 101. The diffraction elements 104 can provide a focal point of far, intermediate, and/or near distance. In some embodiments, diffraction elements 104 are not limited to concentric circular or annular ring-shaped zones, but can include concentric elliptic or oval shaped zones.

In some embodiments, the optic diameter 106 of lens body 101 can be about 4 to about 8 mm, while the total outer diameter 107 of IOL 100 including the haptics 102 can be about 9 to about 18 mm. Lens body 101 can have a center thickness 110 of about 0.8 to about 1.2 mm. Although the embodiment in FIGS. 1A and 1B deals with a posterior chamber IOL, other ophthalmic lenses, including multifocal diffractive contact lenses or eye glass lenses, could also benefit from the same approach. When used for ophthalmic multifocal contact lenses and spectacle or eye glass lenses, haptics 102 are not provided.

The amount of correction that an ophthalmic lens provides is called optical power, and is expressed in Diopter (D). The optical power is calculated as the inverse of a focal distance f measured in meters, which can be a respective focal distance from the lens to a respective focal point for far, intermediate, or near vision. Lens body 101 in the double-sided aspheric shape of the present disclosure can provide a base optical power of about 10 to about 25 D. In some embodiments, lens body 101 can provide a base optical power of about 12, 14, 16, 18, 20, 22, or 24 D. The plurality of diffractive elements 104 can provide added power of $f_1=f_0+2.2D$ and $f_2=f_0+3.3D$.

IOLs can be made of flexible material which permits a reduction of their overall apparent girth by temporary deformation, facilitating their insertion through the cornea, thereby advantageously enabling the use of a corneal incision of concomitantly reduced size. In some embodiments, the lens body can include polypropylene, polycarbonate, polyethylene, acryl-butadiene styrene, polyamide, polychlorotrifluoroethylene, polytetrafluoroethylene, polyvinyl chloride, polyvinylidene fluoride, polyvinylchloride, polydimethylsiloxane, polyethylene terephthalate, ethylene tetrafluoroethylene, ethylene chlorotrifluoroethylene, perfluoroalkoxy, polymethylpentene, polymethylmethacrylate, polystyrene, polyetheretherketone, tetrafluoroethylene, polyurethane, poly(methyl methacrylate), poly (2-hydroxyethyl methacrylate), nylon, polyether block amide, silicone or a mixture thereof.

In some embodiments, the lens body can include a hydrophilic polymer made of monomers selected from the group consisting of: 2-acrylamido-2-methylpropane sulfonic acid, 2-hydroxyethyl methacrylate, N-vinylpyrrolidone, vinylbenzyltrimethyl ammonium salt, diethylaminoethyl methacrylate, dimethylaminoethyl acrylate, dimethylaminoethyl methacrylate, diethyl aminoethyl acrylate, diethylaminomethyl methacrylate, tertiary butylaminoethyl acrylate, tertiary-butylaminoethyl methacrylate and dimethylaminopropylacrylamide, acrylic acid, methacrylic acid, styrenesulfonic acid and salts thereof, hydroxypropyl acrylate, vinylpyrrolidone, dimethylacrylamide, ethylene glycol monomethacrylate, ethylene glycol monoacrylate, ethylene glycol dimethacrylate, ethylene glycol diacrylate, triethylene glycol diacrylate and triethylene glycol methacrylate. In some embodiments, these hydrophilic monomers are surface grafted onto the polymeric matrix in the previous paragraph to make the lens body. In some embodiments, the IOL of the present disclosure can be made of polymeric compositions according to U.S. Pat. No. 10,494,458, which is incorporated herein by reference in its entirety.

The haptics of the IOL according to the present disclosure can be made of polymeric materials including, but not limited to polymethacrylate, polypropylene, polyethylene, polystyrene, and polyacrylate.

The surface of the IOL can include a spheric, aspheric, or toric element. Spheric surfaces can cause spherical aberration, which is a type of optical imperfection that can cause increased glare, and reduced overall quality of vision especially in low light and darkness. Aspheric lenses can correct spherical aberration. Aspherical IOL can provide improved contrast sensitivity, enhanced functional vision and superior night driving ability.

A toric element is typically used for astigmatic eye correction. Generally, astigmatism is an optical defect in which vision is blurred due to the ocular inability to focus a point object into a sharply focused image on the retina. This may be due to an irregular curvature of the cornea and/or lens. The refractive error of the astigmatic eye stems from a difference in degree of curvature, and therefore in degree of refraction, of the different meridians of the cornea and/or the crystalline lens, which causes the eye to have two focal points, one correspondent to each meridian. As used herein, a meridian includes one of two axes that subtend a curved surface, such as the prime meridian on the earth, for example. Meridians may be orthogonal. By way of example, the meridians of the earth may be any orthogonal line of longitude and any line of latitude that curve about the surface of the earth.

For example, in an astigmatic eye, an image may be clearly focused on the retina in the horizontal (sagittal) plane, but may be focused behind the retina in the vertical (tangential) plane. In the case where the astigmatism results only from the cornea, the two astigmatism meridians may be the two axes of the cornea. If the astigmatism results from the crystalline lens, the two astigmatism meridians may be the two axes of the crystalline lens. If the astigmatism results from a combination of the cornea and the crystalline lens, the two astigmatism meridians may be the respective axes of the combined lenses of the cornea and the crystalline lens.

An astigmatism arising from the cornea or crystalline lens, or the combination of the two lenses, may be corrected by a lens including a toric component. A toric surface resembles a section of the surface of a football, for which there are two regular radii of curvature, one smaller than another. These radii may be used to correct the defocus in the two meridians of the astigmatic eye. Thus, blurred vision caused by astigmatism may be corrected by corrective lenses or laser vision correction, such as glasses, hard contact lenses, contact lenses, and/or an IOL, providing a compensating optic specifically rotated around the optical axis.

In some embodiments, the IOL according to the present disclosure can provide far vision for viewing objects at distances ranging from about infinity to about 4 meters (m). In some embodiments, the IOL of the present disclosure can provide near vision for viewing objects at distances less than about 0.4 m. In some embodiments, the IOL of the present disclosure can provide intermediate vision for viewing objects at distances in a range of about 0.4 to about 1 m, about 2 m, about 3 m, or about 4 m. As a result, the IOL of the present disclosure can advantageously provide a degree of accommodation for different distance ranges, typically referred to as pseudo-accommodation. In some embodiments, when implanted into a patient's eye, the combined power of the eye's cornea and the near, intermediate, and far power of the IOL of the present disclosure can allow focusing light emanating from objects within a near, an intermediate, and a far distance range of the patient onto the retina. In some embodiments, the distance focus ($f_0$), intermediate focus ($f_1$), and near focus ($f_2$) provided by the IOL of the present disclosure can have the following ranges:

$$0D \leq \frac{1}{f_0} \leq 55D, 1D \leq \frac{1}{f_1} - \frac{1}{f_0} \leq 2.5D, \text{ and } 2D \leq \frac{1}{f_2} - \frac{1}{f_0} \leq 5D.$$

Figure 2A:
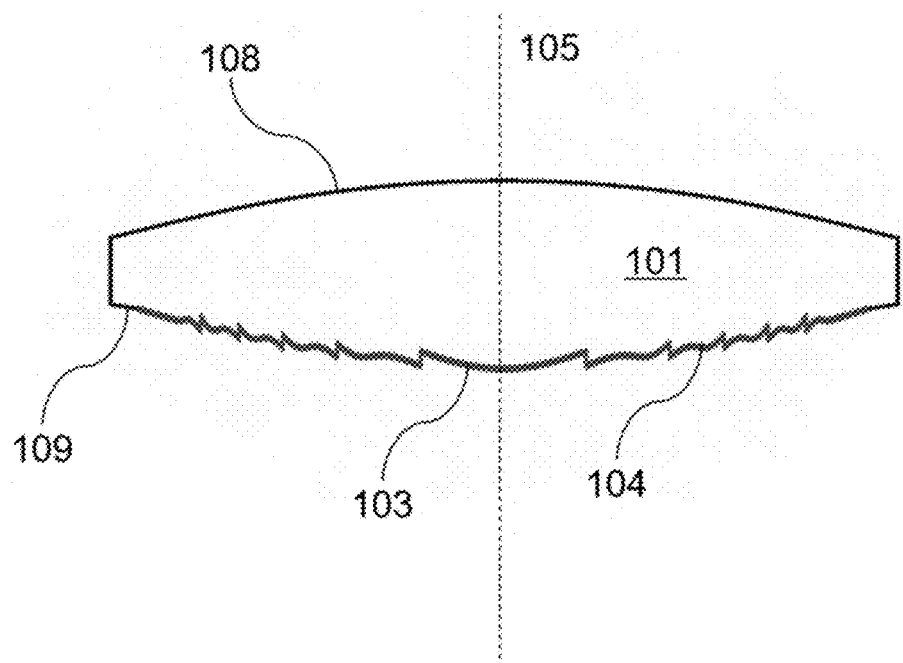
FIG. 2A illustrates a blow-up view of the lens body of the IOL, according to some embodiments of the present disclosure.
Figure 2B:
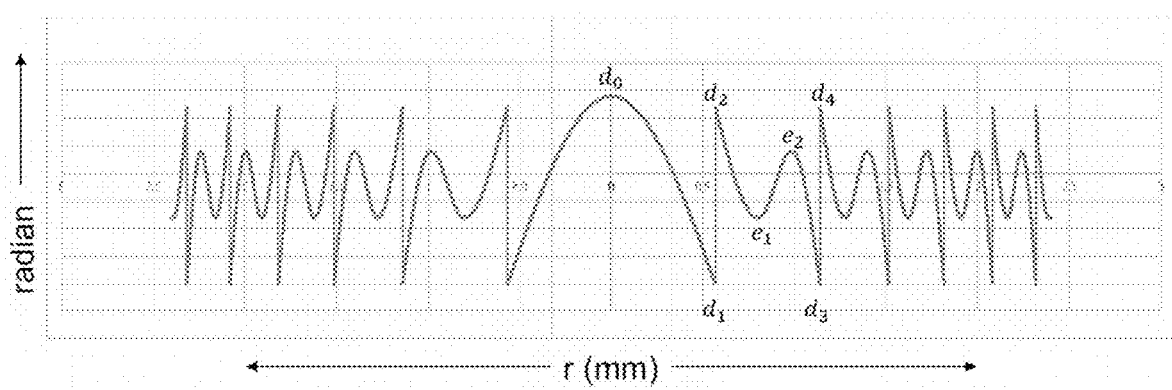
FIG. 2B illustrates the height profile of the diffractive elements, according to some embodiments of the present disclosure.
Figure 2C:
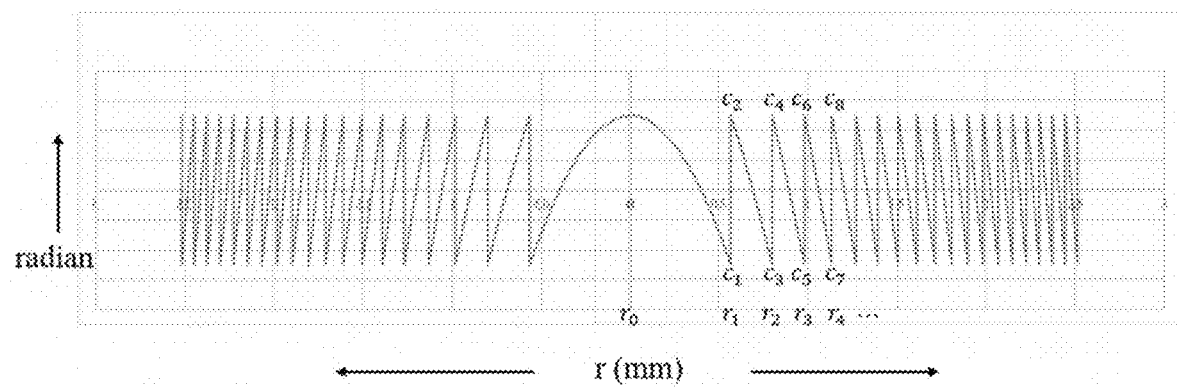
FIG. 2C illustrates the height profile of the diffractive elements, according to another embodiment of the present disclosure.

FIG. 2A shows a blow-up view of lens body 101, including anterior surface 108, posterior surface 109, optical axis 105, central zone 103 and the plurality of diffraction elements 104 generated on the posterior surface. The central zone 103 and diffraction elements 104 are further illustrated in FIG. 2B. The central zone begins from the $0^{th}$ Fresnel zone (from $d_0$ to $d_1$). The diffraction elements are configured as periodically structured smooth curve (from $d_2$ to $d_3$), each periodic structure of the diffraction elements contains two smooth turning points ($e_1$, $e_2$) in between two sharp turning points ($d_2$, $d_3$). FIG. 2C illustrates another embodiment of the present disclosure, by smoothing out two smooth turning points ($e_1$, $e_2$), and their periodically corresponding turning points.

This diffractive structure embodied on the IOLs of the present disclosure can be designed using Equations (I) to (IV) as discussed below.

Pupil Function. A pupil function is a lens characteristic function that describes the physical effect of a lens by which it is possible to change the state of light made incident on the lens, and in specific terms, is represented by the product of the amplitude function A(r) and the exponential function of the phase function $\Phi_{(n)}(r)$ as noted in Equation (I) below.

$$T(r) = A(r)e^{i(\Phi_{(n)}(r))} \quad \text{Equation (I)}$$

T(r): pupil function
A(r): amplitude function
$\Phi_{(n)}(r)$: phase function
n: natural number Phase Function. A phase function is defined as the function that mathematically expresses the physical effect provided in a lens such as giving changes in the phase of incident light on a lens (position of wave peaks and valleys) using any method. The variable of the phase function is mainly expressed by position r in the radial direction from the center of the lens, and the phase of light made incident on the lens at the point of the position r undergoes a change by the phase function $\Phi_{(n)}(r)$ and is emitted from the lens. In specific terms, this is represented by an r-$\Phi$ coordinate system. In the present disclosure, phase is noted as $\Phi$, and the unit is radians. One wavelength of light is represented as $2\pi$ radians, and a half wavelength as $\pi$ radians, for example. A distribution of phase in the overall area in which the phase function is provided expressed in the same coordinate system is called a phase profile, or is simply called a profile or zone profile. With an r axis of $\Phi=0$ as a reference line, this means that the light made incident at the point of $\Phi=0$ is emitted without changing the phase. Also, for this reference line, when a positive value is used for $\Phi$, this means that progress of the light is delayed by that phase amount, and when a negative value is used for $\Phi$, this means that progress of the light is advanced by that phase amount. In an actual ophthalmic lens, a refracting surface for which a diffractive structure is not given corresponds to this reference line (surface). Light undergoes a phase change based on this phase function and is emitted from the lens.

Amplitude Function. An amplitude function is the function expressed by A(r) in Equation (I) noted above. In the present disclosure, this is defined as a function that represents the change in the light transmission amount when passing through a lens. The variable of the amplitude function is represented as position r in the radial direction from the center of the lens, and represents the transmission rate of the lens at the point of position r. Also, the amplitude function is in a range of 0 or greater and 1 or less, which means that light is not transmitted at the point of A(r)=0, and that incident light is transmitted as it is without loss at the point of A(r)=1.

Zone. In the present disclosure, a zone is used as the minimum unit in a diffractive structure, element, or diffraction grating provided in a lens.

The height profile of the diffractive structure ($Z_{diff}$) on the IOL can be calculated based on Equation (II) below.

$$Z_{diff}(r) = \Phi_{(n)}(r) \times \frac{\lambda}{n_1 - n_0} \qquad \text{Equation (II)}$$

$Z_{diff}(r)$: height profile of the diffractive structure
$\Phi_{(n)}(r)$: phase function
$\lambda$: design wavelength
$n_1$: refractive index of the lens material
$n_0$: refractive index of the medium covering the lens The radius of a particular diffractive zone ($r_n$) can be calculated based on Equation (III) below.

$$r_n = \sqrt{2 \times \lambda \times n \times f} \qquad \text{Equation (III)}$$

$r_n$: radius of the $n^{th}$ zone
$\lambda$: design wavelength
f: reciprocal of add power Phase function ($\Phi_{(n)}(r)$) can be calculated via Equation (IV) below.

$$\Phi_{(n)}(r) = A \times \sin\left(\left(B \times \frac{r - r_n}{r_{n+1} - r_n} + C\right) \times \pi\right) + D \qquad \text{Equation (IV)}$$

$\Phi_{(n)}(r)$: phase function
r: is the radial distance from a center of lens
$r_n$: radius of the $n^{th}$ zone
$r_{n+1}$: radius of the $(n+1)^{th}$ zone
wherein A, B, C and D, are the light distribution parameters. A is the amplitude; B is the period as $$\frac{2\pi}{B};$$

C is the phase shift, if it is +C, it shifts left, if the phase shift is -C, it shifts right; D is the vertical shift, if it is +D, the function moves up, if it is -D, then the function moves down.

The double-sided aspheric structure (anterior and posterior of the optic area of the IOL) is for the correction of the spherical aberration of the lens. The height profile of the aspheric base structure ($Z_{asp}$) of the lens can be calculated according to the following Equation (V):

$$Z_{asp}(r) = \frac{cr^2}{1 + \sqrt{1-(1+k)c^2r^2}} + \sum_{i=2}^{n} A_i r^{2i} \qquad \text{Equation (V)}$$

$Z_{asp}$: is the height profile of the aspheric structure
r: is the radial distance from a center of lens
k: is the conic constant
c: is the curvature
$A_i$: is the high order aspheric coefficient When both aspheric and diffractive structures are placed onto the same surface (anterior surface and/or posterior surface of the IOL), according to some embodiments of the present disclosure, the height profile of the combination structure ($Z_{total}$) will be the summation of the height profile of the aspheric structure ($Z_{asp}$) and the height profile of the diffractive structure ($Z_{diff}$), as calculated according to the below Equation (VI).

$$Z_{total}(r) = Z_{asp}(r) + Z_{diff}(r) \qquad \text{Equation (VI)}$$

$Z_{diff}$: height profile of the diffractive structure
$Z_{aspheric}$: height profile of the aspheric structure
$Z_{total}$: height profile of the combination structure, i.e. the lens body In some embodiments, the above-described lens can be contact lens or IOL. In some embodiments, the IOL can be intracorneal IOL, anterior chamber IOL or posterior chamber IOL. In some embodiments, the IOL can be posterior chamber IOL. While the haptic arms are illustrated in the embodiment, any suitable haptics fixation structure for the capsular bag or the ciliary sulcus compatible with posterior chamber implantation can also be used in a posterior chamber IOL.

A way of estimating the optical priority of an intraocular lens comprises determining experimentally its modulation transfer function (MTF). The MTF of an optical system can be measured according to Annex C of ISO 11979-2, which reflects the proportion of the contrast which is transmitted through the optical system for a determined spatial frequency of a test pattern, which frequency is defined as "cycles/mm" or "LP/mm", in which "LP" indicates "line pairs." Generally, the contrast decreases with an increase in spatial frequency.

All publications, patents, and patent applications mentioned in the present disclosure are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, it will be understood that modifications and variations are encompassed within the spirit and scope of the instant disclosure. The preferred methods and materials are now described.

Presented below are examples discussing different embodiments of the IOLs contemplated for the discussed applications. The following examples are provided to further illustrate the embodiments of the present disclosure, but are not intended to limit the scope of the disclosure. While they are typical of those that might be used, other procedures, methodologies, or techniques known to those skilled in the art may alternatively be used.

EXAMPLES

Example 1

Figure 3A:
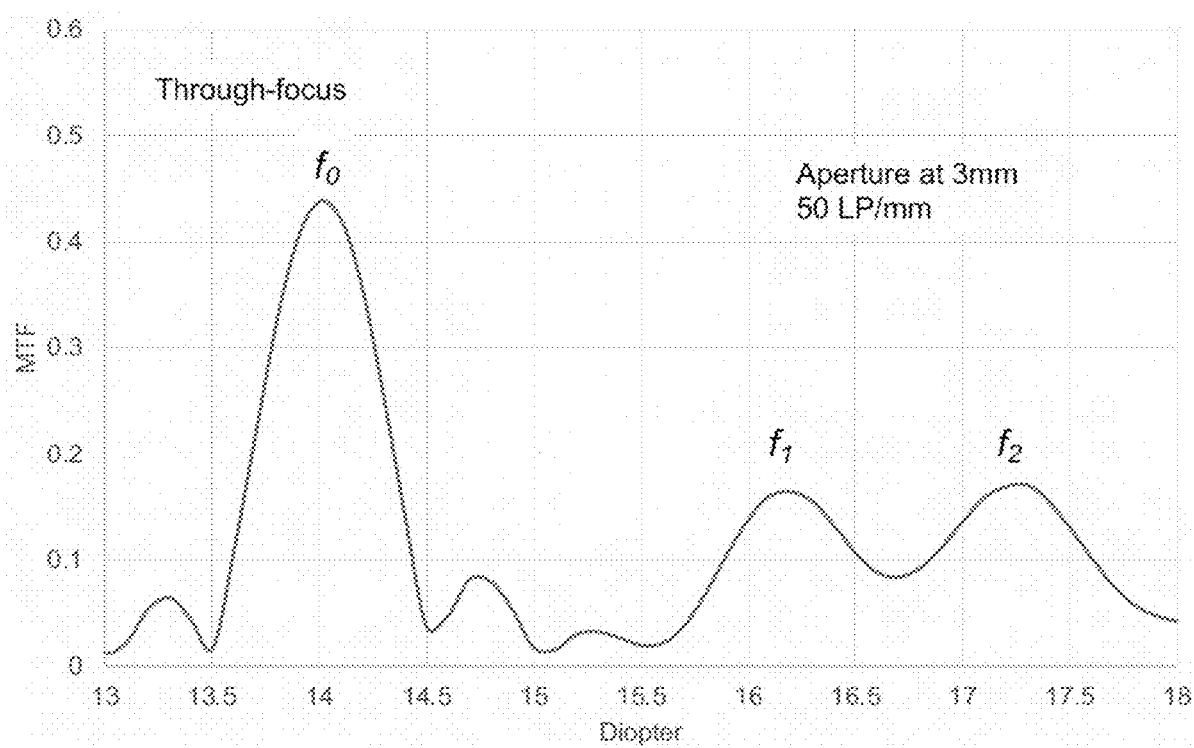
FIG. 3A illustrates the optical performance (modulation transfer function, MTF) at a 3 mm aperture and at a resolution measurement of 50 LP/mm by varying parameters according to a first embodiment of the present disclosure.

MTF and Height Profile of the IOL According to the First Embodiment of the Present Disclosure From Equation (IV), by varying parameters A, B, C and D, and controlling the distance focus ($f_0$), the intermediate focus ($f_1$), and the near focus ($f_2$), the optical performance (modulation transfer function, MTF) at a 3 mm aperture and at a resolution measurement of 50 line pairs per millimeter (LP/mm) is shown in FIG. 3A. The parameters of A, B, C and D are varied according to Table 1 below.

TABLE 1

Variation of parameters A-D in a first embodiment of the present disclosure.

|  | A | B | C | D |
|---|---|---|---|---|
| Ring 1 | 0.6 | 0.5 | 1 | −0.42 |
| Ring 2 | 0.41 | 0.5 | 0.5 | 0.24 |
| Ring 3 | −0.1 | 1 | 0.5 | −0.07 |
| Ring 4 | 0.45 | 0.5 | 1 | −0.42 |
| Ring 5 | 0.41 | 0.5 | 0.5 | 0.24 |
| Ring 6 | −0.1 | 1 | 0.5 | −0.07 |
| Ring 7 | 0.45 | 0.5 | 1 | −0.42 |
| Ring 8 | 0.41 | 0.5 | 0.5 | 0.24 |
| Ring 9 | −0.1 | 1 | 0.5 | −0.07 |
| Ring 10 | 0.45 | 0.5 | 1 | −0.42 |
| Ring 11 | 0.41 | 0.5 | 0.5 | 0.24 |
| Ring 12 | −0.1 | 1 | 0.5 | −0.07 |
| Ring 13 | 0.45 | 0.5 | 1 | −0.42 |
| Ring 14 | 0.41 | 0.5 | 0.5 | 0.24 |
| Ring 15 | −0.1 | 1 | 0.5 | −0.07 |

The curve in FIG. 3A shows three peaks corresponding to a distance focus at about 14.0 D, an intermediate focus at about 16.2 D, and a near focus at about 17.3 D, respectively. The minimum value between $f_1$ and $f_2$ is about 50% of the MTF of $f_1$.

Figure 3B:
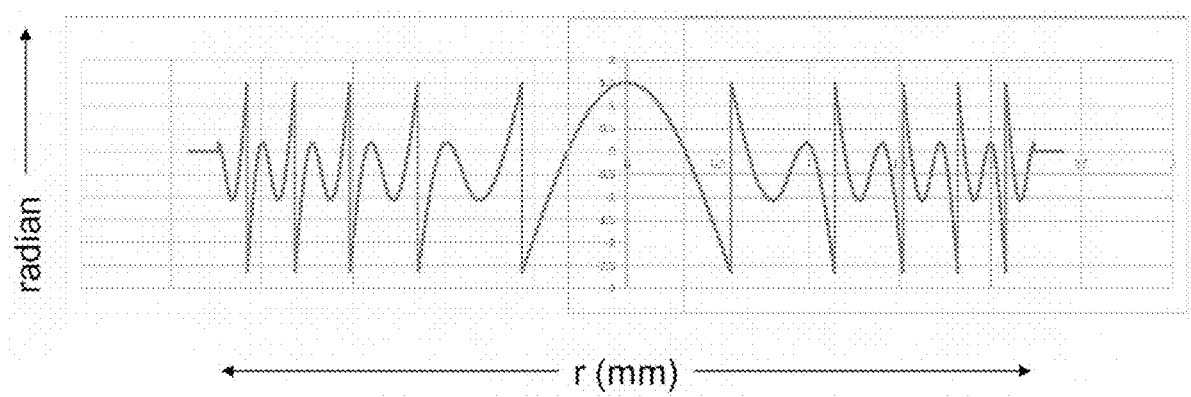
FIG. 3B illustrates the height profile of the aspheric and diffractive combination structure according to a first embodiment of the present disclosure.

The $Z_{total}(r)$ height profile of the aspheric and diffractive combination structure is shown in FIG. 3B. The height is depicted at μm scale along the vertical axis. The optical axis, running through the center of the lens body, is assumed to be at a radial position r=0, whereas the radial distance r measured in outward direction from the optical axis is expressed in mm along the vertical axis.

Example 2

Figure 4A:
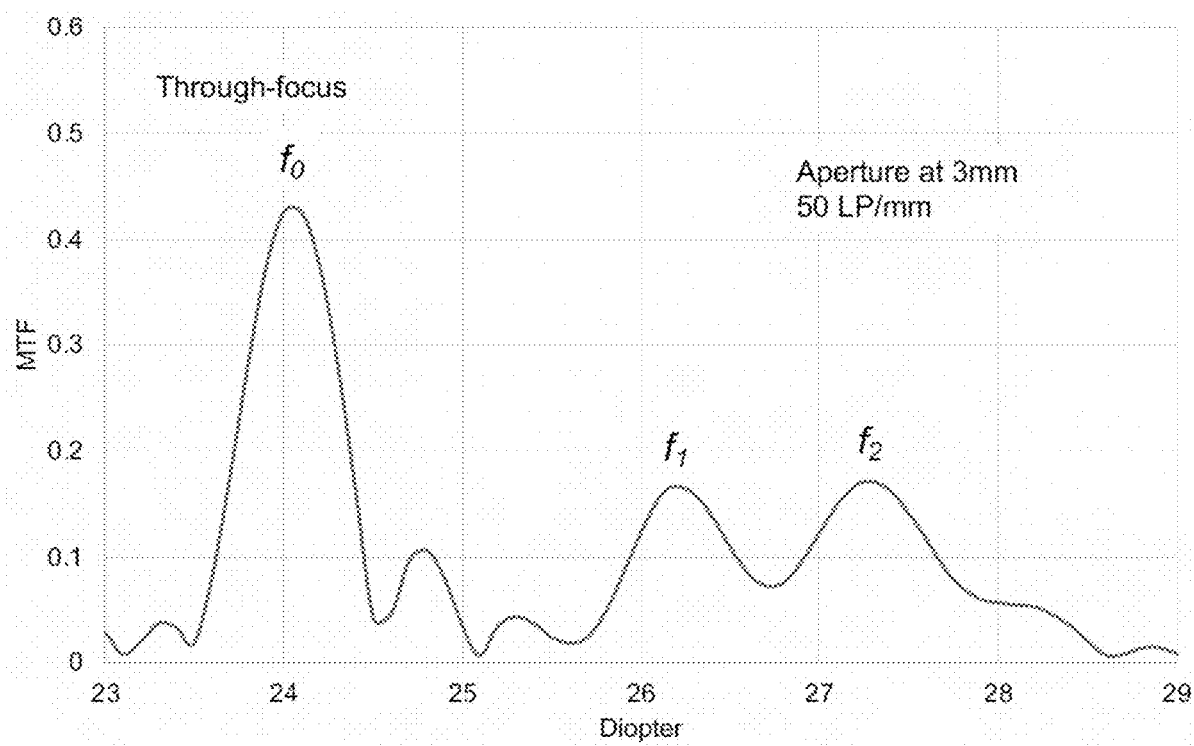
FIG. 4A illustrates the optical performance (MTF) at a 3 mm aperture and at a resolution measurement of 50 LP/mm by varying parameters according to a second embodiment of the present disclosure.
Figure 4B:
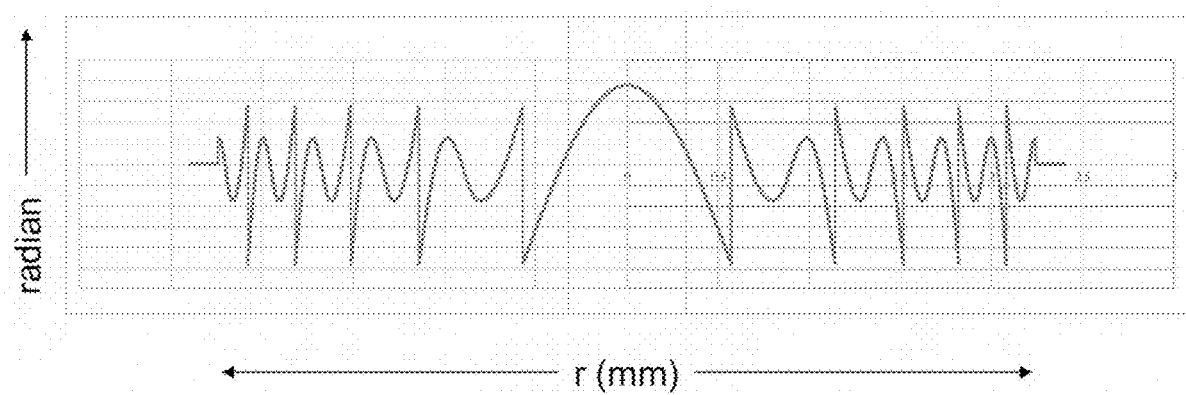
FIG. 4B illustrates the height profile of the aspheric and diffractive combination structure according to a second embodiment of the present disclosure.

MTF and Height Profile of the IOL According to the Second Embodiment of the Present Disclosure From Equation (IV), by varying parameters A, B, C and D, and controlling the $f_0$, $f_1$ and $f_2$, the optical performance (MTF) at a 3 mm aperture and at a resolution measurement of 50 line pairs per millimeter (LP/mm) is shown in FIG. 4A. The parameters of A, B, C and D are varied according to Table 2 below. The $Z_{total}(r)$ height profile of the aspheric and diffractive combination structure is shown in FIG. 4B.

TABLE 2

Variation of parameters A-D in a second embodiment of the present disclosure.

|  | A | B | C | D |
|---|---|---|---|---|
| Ring 1 | 0.68 | 0.5 | 1 | −0.38 |
| Ring 2 | 0.36 | 0.5 | 0.5 | 0.22 |
| Ring 3 | −0.12 | 1 | 0.5 | −0.02 |
| Ring 4 | 0.48 | 0.5 | 1 | −0.38 |
| Ring 5 | 0.36 | 0.5 | 0.5 | 0.22 |
| Ring 6 | −0.12 | 1 | 0.5 | −0.02 |
| Ring 7 | 0.48 | 0.5 | 1 | −0.38 |
| Ring 8 | 0.36 | 0.5 | 0.5 | 0.22 |
| Ring 9 | −0.12 | 1 | 0.5 | −0.02 |
| Ring 10 | 0.48 | 0.5 | 1 | −0.38 |
| Ring 11 | 0.36 | 0.5 | 0.5 | 0.22 |
| Ring 12 | −0.12 | 1 | 0.5 | −0.02 |
| Ring 13 | 0.48 | 0.5 | 1 | −0.38 |
| Ring 14 | 0.36 | 0.5 | 0.5 | 0.22 |
| Ring 15 | −0.12 | 1 | 0.5 | −0.02 |

The curve in FIG. 4A shows three peaks corresponding to a distance focus at about 24.0 D, an intermediate focus at about 26.2 D, and a near focus at about 27.3 D, respectively. The minimum value between $f_1$ and $f_2$ is about 50% of the MTF of $f_1$.

Example 3

Figure 5A:
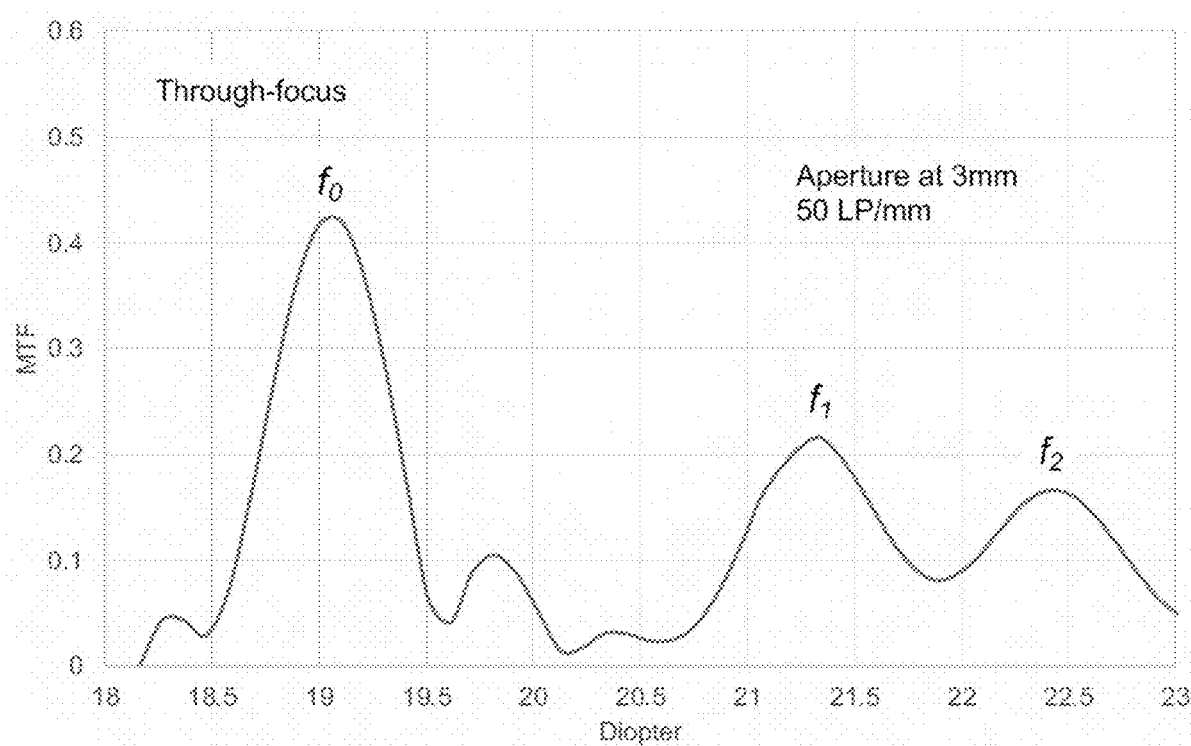
FIG. 5A illustrates the optical performance (MTF) at a 3 mm aperture and at a resolution measurement of 50 LP/mm by varying parameters according to a third embodiment of the present disclosure.
Figure 5B:
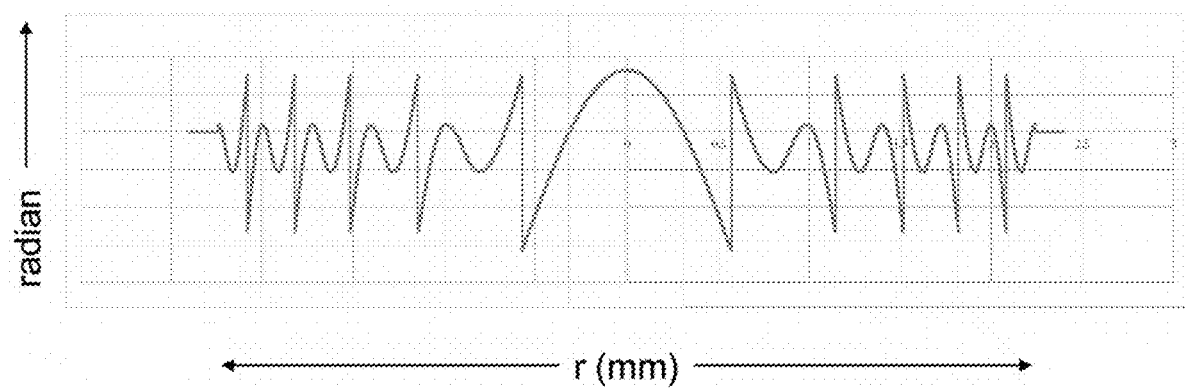
FIG. 5B illustrates the height profile of the aspheric and diffractive combination structure according to a third embodiment of the present disclosure.

MTF and Height Profile of the IOL According to the Third Embodiment of the Present Disclosure From Equation (IV), by varying parameters A, B, C and D, and controlling the $f_0$, $f_1$ and $f_2$, the optical performance (MTF) at a 3 mm aperture and at a resolution measurement of 50 line pairs per millimeter (LP/mm) is shown in FIG. 5A. The parameters of A, B, C and D are varied according to the Table 3 below. The $Z_{total}(r)$ height profile of the aspheric and diffractive combination structure is shown in FIG. 5B.

TABLE 3

Variation of parameters A-D in a third embodiment of the present disclosure.

|  | A | B | C | D |
|---|---|---|---|---|
| Ring 1 | 0.76 | 0.5 | 1 | −0.5 |
| Ring 2 | 0.41 | 0.5 | 0.5 | 0.24 |
| Ring 3 | −0.1 | 1 | 0.5 | −0.07 |
| Ring 4 | 0.45 | 0.5 | 1 | −0.42 |
| Ring 5 | 0.41 | 0.5 | 0.5 | 0.24 |
| Ring 6 | −0.1 | 1 | 0.5 | −0.07 |
| Ring 7 | 0.45 | 0.5 | 1 | −0.42 |
| Ring 8 | 0.41 | 0.5 | 0.5 | 0.24 |
| Ring 9 | −0.1 | 1 | 0.5 | −0.07 |
| Ring 10 | 0.45 | 0.5 | 1 | −0.42 |
| Ring 11 | 0.41 | 0.5 | 0.5 | 0.24 |

TABLE 3-continued

Variation of parameters A-D in a third embodiment of the present disclosure.

|  | A | B | C | D |
|---|---|---|---|---|
| Ring 12 | −0.1 | 1 | 0.5 | −0.07 |
| Ring 13 | 0.45 | 0.5 | 1 | −0.42 |
| Ring 14 | 0.41 | 0.5 | 0.5 | 0.24 |
| Ring 15 | −0.1 | 1 | 0.5 | −0.07 |

The curve in FIG. 5A shows three peaks corresponding to a distance focus at about 19.0 D, an intermediate focus at about 21.2 D, and a near focus at about 22.3 D, respectively.

Figure 6:
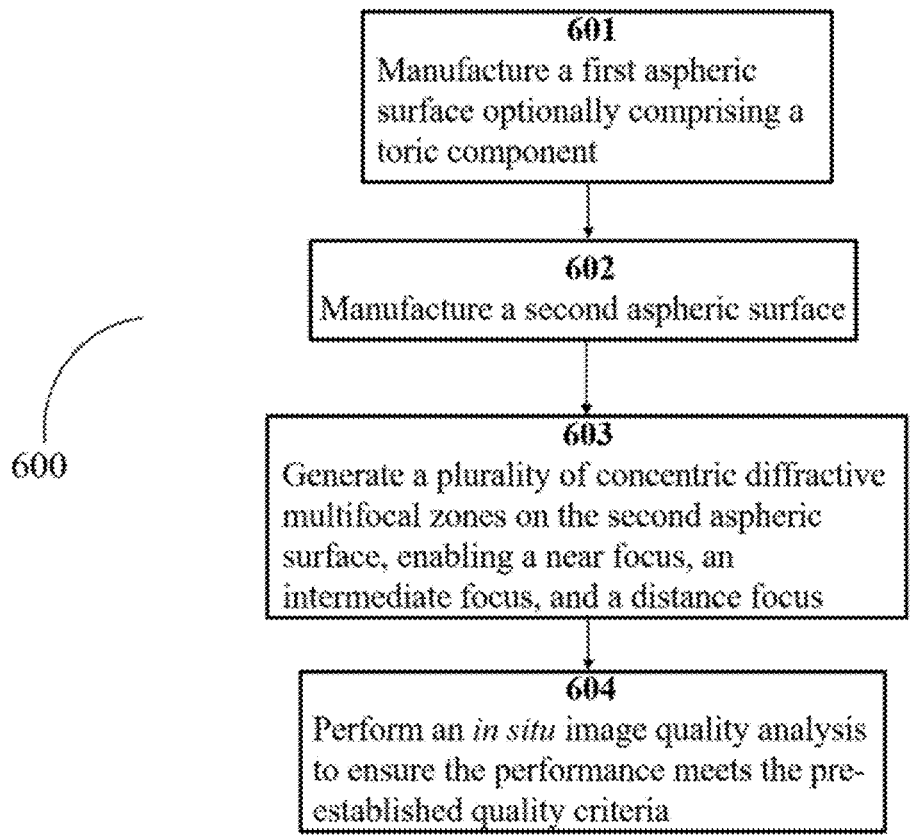
FIG. 6 is a flowchart illustrating the design and manufacture of the double-sided aspheric multifocal diffractive IOL, according to some embodiments of the present disclosure.

FIG. 6 is a flowchart 600 illustrating the design and manufacture of the double-sided aspheric multifocal diffractive IOL, according to some embodiments of the present disclosure. Step 601 manufactures a first aspheric surface optionally including a toric component. Step 602 manufactures a second aspheric surface. Step 603 generates a plurality of concentric diffractive multifocal zones on the second aspheric surface to produce a near focus, an intermediate focus, and a distance focus. Step 604 performs an in situ image quality analysis of the double-sided aspheric diffractive multifocal lens on an ISO Model Eye 2 to measure the through focus MTF using the TRIOPTICS OptiSpheric® IOL PRO 2 up to the pre-established performance criteria.

While the disclosure has been particularly shown and described with reference to specific embodiments, it should be understood by those having skill in the art that various changes in form and detail may be made therein without departing from the spirit and scope of the present disclosure as disclosed herein.

All references referred to in the present disclosure are hereby incorporated by reference in their entirety. Various embodiments of the present disclosure may be characterized by the potential claims listed in the paragraphs following this paragraph (and before the actual claims provided at the end of this application). These potential claims form a part of the written description of this application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public.

The embodiments of the disclosure described above are intended to be merely exemplary; numerous variations and modifications will be apparent to those skilled in the art. All such variations and modifications are intended to be within the scope of the present disclosure as defined in any appended claims.

What is claimed is:

1. A diffractive trifocal lens comprising a lens body, the lens body comprising:
(a) a first aspheric surface; and
(b) a second aspheric surface comprising a central zone and a plurality of diffractive elements comprising concentric annular zones extending in a radial direction, each concentric annular zone having a periodically structured curve comprising two smooth turning points between two sharp turning points, wherein a slope of the periodically structured curve changes sign at each of the two smooth turning points in each of the concentric annular zones, thereby producing a near focus ($f_2$), an intermediate focus ($f_1$), and a distance focus ($f_0$),
wherein a modulation transfer function (MTF) of the diffractive trifocal lens comprises a first peak at the intermediate focus ($f_1$) and a second peak at the near focus ($f_2$), and
wherein a most minimum value of the MTF between the first peak and the second peak is about 50% of a most maximum value of the MTF at the first peak, thereby improving vision contrast between the intermediate focus ($f_1$) and the near focus ($f_2$); and
wherein:
an optical power of the distance focus ($f_0$) is greater than or equal to 0 diopters and less than or equal to 55 diopters;
an optical power of the intermediate focus ($f_1$) is greater than the optical power of the distance focus ($f_0$) by a first difference in optical power that is greater than or equal to 1 diopter and less than or equal to 2.5 diopters; and
an optical power of the near focus ($f_2$) is greater than the optical power of the distance focus ($f_0$) by a second difference in optical power that is greater than or equal to 2 diopters and less than or equal to 5 diopters.

2. The diffractive trifocal lens of claim 1, wherein the first aspheric surface is anterior surface.

3. The diffractive trifocal lens of claim 1, wherein the second aspheric surface is posterior surface.

4. The diffractive trifocal lens of claim 1, wherein the first aspheric surface comprises a toric component.

5. The diffractive trifocal lens of claim 1, wherein the diffractive trifocal lens is an intraocular lens (IOL) sized for insertion into a human eye.

6. The diffractive trifocal lens of claim 5, further comprising a pair of haptics extended outwardly from the lens body.

7. The diffractive trifocal lens of claim 5, wherein the IOL is sized for insertion into a posterior chamber of the human eye.

8. The diffractive trifocal lens of claim 7, wherein the posterior chamber IOL is configured to be implanted into a capsular bag of the human eye.

9. A method of treating an ophthalmic disease or disorder in a subject, the method comprising implanting into an eye of the subject the diffractive trifocal lens of claim 1.

10. The method of claim 9, wherein the ophthalmic disease or disorder is selected from the group consisting of cataract and presbyopia.

11. The method of claim 9, wherein the diffractive trifocal lens is an intraocular lens (IOL) sized for insertion into the subject's eye.

12. The method of claim 11, wherein the diffractive trifocal lens further comprises a pair of haptics extended outwardly from the lens body.

13. The method of claim 11, wherein the IOL is implanted into a capsular bag of the subject's eye.

14. A method of manufacturing the diffractive trifocal lens of claim 1, the method comprising:
(a) manufacturing the first aspheric surface optionally comprising a toric component;
(b) manufacturing the second aspheric surface; and
(c) generating the central zone and the diffractive elements comprising the plurality of concentric annular zones on the second aspheric surface, each concentric annular zone having the periodically structured curve comprising the two smooth turning points between the two sharp turning points, wherein the slope of the periodically structured curve changes sign at each of the two smooth turning points in each of the concentric annular zones, thereby producing the near focus ($f_2$), the intermediate focus ($f_1$), and the distance focus ($f_0$).

15. The method of claim 14, further comprising:

performing an in situ image quality analysis to measure the modulation transfer function (MTF) of the trifocal lens using pre-established quality criteria.

\* \* \* \* \*